United States Patent [19]

O'Doherty et al.

[11] Patent Number: 4,468,380

[45] Date of Patent: Aug. 28, 1984

[54] ANTICOCCIDIAL COMBINATIONS COMPRISING POLYETHER ANTIBIOTICS AND CARBANILIDES

[75] Inventors: George O. P. O'Doherty, Greenfield; Albert J. Clinton, Indianapolis, both of Ind.

[73] Assignee: Eli Lilly and Company, Indianapolis, Ind.

[21] Appl. No.: 260,962

[22] Filed: May 6, 1981

Related U.S. Application Data

[63] Continuation of Ser. No. 107,304, Dec. 26, 1979, abandoned.

[51] Int. Cl.$^3$ .................... A61K 35/00; A61K 31/35
[52] U.S. Cl. .................................. 424/114; 424/115; 424/283; 424/322
[58] Field of Search ............... 424/114, 115, 283, 322

[56] References Cited

U.S. PATENT DOCUMENTS

| | | | |
|---|---|---|---|
| 3,284,433 | 11/1966 | Becker et al. | 424/322 |
| 3,501,568 | 2/1975 | Haney et al. | 424/115 |
| 3,555,150 | 1/1971 | Gorman et al. | 424/122 |
| 3,577,531 | 5/1971 | Gorman et al. | 424/122 |
| 3,627,883 | 12/1971 | Gorman et al. | 424/122 |
| 3,761,594 | 9/1973 | Challey | 424/258 |
| 3,839,559 | 10/1974 | Hamill et al. | 424/121 |
| 3,864,479 | 2/1975 | Miller et al. | 424/185 |
| 3,867,544 | 2/1975 | Stevenson | 424/322 |
| 4,061,755 | 12/1977 | McDougald | 424/263 |
| 4,075,323 | 2/1978 | McDougald | 424/114 |
| 4,083,962 | 4/1978 | McDougald | 424/114 |
| 4,130,661 | 12/1978 | Kulsa et al. | 424/324 |
| 4,218,438 | 8/1980 | Callender | 424/181 |

FOREIGN PATENT DOCUMENTS

| | | |
|---|---|---|
| 2334355 | 1/1975 | Fed. Rep. of Germany . |
| 1339467 | 12/1973 | United Kingdom . |
| 1463519 | 2/1977 | United Kingdom . |

OTHER PUBLICATIONS

Chem. Abst., 8th Coll. Index, vol. 66–75, (1967–1971), pp. 6304S–6305S.
Science 122, 244–245 (1955).
"Control of Coccidiosis in Broiler Chickens" Kingston–D.M.V. thesis, University of Sydney, Australia.

*Primary Examiner*—Sam Rosen
*Attorney, Agent, or Firm*—Kathleen R. S. Page; Arthur R. Whale

[57] ABSTRACT

The present invention is directed to novel anticoccidial compositions and methods of employing the same to control coccidiosis in poultry. These compositions comprise a polyether antibiotic and a second component which is a selected carbanilide.

52 Claims, No Drawings

ANTICOCCIDIAL COMBINATIONS COMPRISING POLYETHER ANTIBIOTICS AND CARBANILIDES

This application is a continuation of application Ser. No. 107,304, filed Dec. 26, 1979, now abandoned.

BRIEF SUMMARY OF THE INVENTION

The present invention is directed to a process for controlling coccidiosis in poultry which comprises orally administering to the poultry a feedstuff comprising a first component which is a polyether antibiotic and a second component which is selected from a group of carbanilides.

The present invention is also directed to the compositions to be employed in the foregoing methods; and to certain of the carbanilides as novel compounds.

DETAILED DESCRIPTION

The polyether antibiotics are a class of antibiotics produced by the Streptomyces genus of microorganisms. They are characterized by comprising a multiplicity of cyclic ethers in their structures. The class is reviewed in Kirk-Othmer: *Encyclopedia of Chemical Technology*, Vol. 3, Third Edition (John Wiley & Sons, Ind., 1978), page 47 et seq.; in *Annual Reports in Medicinal Chemistry* Volume 10 (Academic Press, N.Y. 1975), page 246 et seq.; and in *J. Chrom. Lib.*, Vol. 15 (Elsevier Scientific Publishing Co., N.Y. 1978), page 488 et seq.

Like other products of fermentation origin, many of the polyether antibiotics comprise more than one factor. The various factors are all usable in the present invention. Further, many of these antibiotics readily form ethers, esters, salts, or other derivatives, which are either active as such or are converted in vivo to the basic antibiotic. Such derivatives can also be employed in the present invention. All that is necessary is that an active moiety of a polyether antibiotic be delivered in vivo.

Representative polyether antibiotics include the following: monensin (factors A, B, and C), laidlomycin, nigericin, grisorixin, dianemycin, lenoremycin, salinomycin, narasin, lonomycin, antibiotic X206, alborixin, septamycin, antibiotic 204A, A32887 (K41), etheromycin, lasalocid (factors A, B, C, D, and E), isolasalocid A, lysocellin, and antibiotic A23187.

Preferred polyether antibiotics include monensin, narasin, lasalocid, salinomycin, A-204, lonomycin, X-206, nigericin, and dianemycin, and especially monensin, narasin, lasalocid, and A-204.

Many of the carbanilides to be employed in the present combinations are known compounds, and some of them are known to exhibit anticocidial activity.

The carbanilides can be divided into three groups. A first group consists of the following compounds (literature references, where known, are included):

A. Miscellaneous Carbanilide Compounds

A.1. 3,3'-bis(trifluoromethyl)-4,4'-dichlorocarbanilide (CAS registry #370-50-3; C.A. 68:2655v)
A.2. 3,3',5,5'-tetrakis(trifluoromethyl)carbanilide (CAS registry #3824-74-6; C.A. 66: P646444, C.A. 68: 2655v, and C.A. 71: P91052y)
A.3. 3-chloro-4'-fluorocarbanilide (C.A. 65: 12792c)
A.4. 2-chloro-2'-fluorocarbanilide
A.5. 3,4',5-tris(trifluoromethyl)carbanilide (CAS registry #23747-71-9; C.A. 71: P91056c)
A.6. 3,4,5-trichlorocarbanilide
A.7. 2-chloro-5-(trifluoromethyl)-4'-(ethoxycarbonyl)carbanilide
A.8. 2,6-dimethyl-4'-(N-methylacetamido)carbanilide
A.9. 2-methoxy-4'-acetamidocarbanilide
A.10. 3-(trifluoromethyl)-4'-iodothiocarbanilide
A.11. 2-fluoro-4'-(aminosulfonyl)carbanilide
A.12. 2-methoxy-4'-isopropylcarbanilide
A.13. 2-methyl-2',5'-diethoxycarbanilide
A.14. 4-ethyl-2'-methoxycarbanilide
A.15. 2-methyl-5-chloro-2',5'-dimethoxycarbanilide
A.16. 2,4,4'-trimethyl-3'-nitrocarbanilide
A.17. 2-amino-3-nitro-5-(trifluoromethyl)-2',4'-dimethylcarbanilide
A.18. 2-amino-3,4'-dinitro-5-(trifluoromethyl)-2'-chlorocarbanilide
A.19. 2-amino-3,5'-dinitro-5-(trifluoromethyl)-2'-fluorocarbanilide
A.20. 2-amino-3-nitro-5-(trifluoromethyl)-2'-(ethoxycarbonyl)carbanilide
A.21. 2-ethyl-6-sec-butylcarbanilide
A.22. 2-isopropyl-2',4',6'-trimethylcarbanilide
A.23. 2-amino-3-nitro-3',5-bis(trifluoromethyl)-4'-chlorocarbanilide
A.24. 2-ethyl-6-sec-butyl-4'-n-butoxycarbanilide
A.25. 2-amino-3-nitro-5-(trifluoromethyl)-2',4',5'-trichlorocarbanilide
A.26. 2-amino-3,3'-dinitro-5-(trifluoromethyl)-4'-chlorocarbanilide
A.27. 2-amino-3-nitro-5-(trifluoromethyl)-2'-methyl-4'-bromocarbanilide
A.28. 2-amino-3-nitro-5-(trifluoromethyl)-2',6'-dibromo-4'-fluorocarbanilide
A.29. 2-amino-3-nitro-2',5-bis(trifluoromethyl)-4'-chlorocarbanilide
A.30. 3,3',5,5'-tetrakis(trifluoromethyl)thiocarbanilide (CAS registry #1060-92-0; C.A. 66: 64644H)
A.31. 2,4-dimethoxy-4'-(ethoxycarbonyl)carbanilide
A.32. 4-(ethoxycarbonyl)-2'-methyl-6'-ethylcarbanilide
A.33. 2,2'-dinitro-4,4'-bis(trifluoromethyl)carbanilide (CAS registry #16588-81-1; C.A. 68: 2655v)
A.34. 3,3',4,4',5,5'-hexachlorocarbanilide
A.35. 3-nitro-4-chloro-4'-(trifluoromethyl)carbanilide
A.36. 4-chloro-3,4'-bis(trifluoromethyl)carbanilide (CAS registry #23747-70-8; C.A. 71: P91056c)
A.37. 4,4'-dinitro-2,2'-bis(trifluoromethyl)carbanilide (CAS registry #16588-84-4; C.A. 68: 2655v)
A.38. 4,4'-bis(trifluoromethyl)carbanilide (CAS registry #1960-88-9; C.A. 71: 91056c)
A.39. 3-bromo-3',5'-dimethylcarbanilide
A.40. 2,5-dichloro-4'-methyl-$N^2$-ethylcarbanilide
A.41. 2,5-dichloro-2',4'-difluorocarbanilide
A.42. 2-amino-3-nitro-3',5,5'-tris(trifluoromethyl)carbanilide
A.43. 2,6-diethyl-4'-(ethoxycarbonyl)carbanilide
A.44. 3-ethyl-3'-chloro-4'-methyl-$N^2$-ethylcarbanilide
A.45. 2,6-dimethyl-4'-(ethoxycarbonyl)carbanilide
A.46. 4-methoxy-3'-acetamidocarbanilide
A.47. 2-methoxy-4'-(n-butoxycarbonyl)carbanilide
A.48. 4-(isobutoxycarbonyl)carbanilide
A.49. 2,4'-bis(methoxycarbonyl)carbanilide
A.50. 2',4-dichloro-3-nitro-3'-(trifluoromethyl)carbanilide
A.51. 3,4,4',5-tetrachloro-3'-(trifluoromethyl)carbanilide (C.A. 63: P440f)
A.52. 4-chloro-3-nitro-3',5'-bis(trifluormethyl)carbanilide
A.53. 2,4,6-trimethyl-4'-(ethoxycarbonyl)carbanilide A.54. 2-trifluoromethyl)-2'-ethyl-6'-isopropylcarbanilide
A.55. 4-chloro-3,3',5'-tris(trifluoromethyl)carbanilide (CAS registry #4528-83-0; C.A. 71: 91052y and 66: 64644h)
A.56. 3,4,4',5-tetrachloro-3'-nitrocarbanilide
A.57. 2,6-dimethyl-4'-benzoylcarbanilide
A.58. 3,4-dimethyl-2'-ethoxycarbanilide
A.59. 2-chloro-4,4'-bis(methylthio)carbanilide
A.60. 2-methyl-2'-ethoxycarbanilide
A.61. 4-chloro-2-methoxythiocarbanilide
A.62. 4,4'-dinitro-N,N'-dimethylcarbanilide (CAS registry #34594-47-3; C.A. 83: 36180m and C.A. 85: 20476t)
A.63. 4-(trifluoromethyl)-4'-nitrocarbanilide (CAS registry #23747-76-4 U.S. Pat. No. 3,867,544)
A.64. 3,3',5,5'-tetrakis(trifluoromethyl)-N,N'-dimethylcarbanilide A second group of carbanilides to be employed in the present combinations is the group of carbanilides described by U.S. Pat. No. 3,284,433. These compounds are of the formula

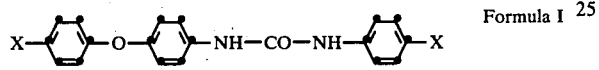

Formula I wherein each X is independently selected from the group consisting of chlorine, bromine, and nitro radicals; and (2) compounds of the same formula as (I) except that a hydrogen of at least one of the rings of (I) is replaced by a substituent selected from the group consisting of chlorine, bromine, nitro and lower alkyl radicals.

Representative compounds of this group include the following:

B. Phenoxycarbanilides of U.S. Pat. No. 3,284,433

B.1. 4-nitro-4'-(4-chlorophenoxy)carbanilide
B.2. 4-nitro-4'-(3,4-dichlorophenoxy)carbanilide
B.3. 4-nitro-3'-chloro-4'-(4-chlorophenoxy)carbanilide
B.4. 4-nitro-3',5'-dichloro-4'-(4-chlorophenoxy)carbanilide
B.5. 4-nitro-3'-chloro-4'-(3,4-dichlorophenoxy)carbanilide
B.6. 4-nitro-4'-(2,4-dichlorophenoxy)carbanilide
B.7. 4-nitro-4'-(4-nitrophenoxy)carbanilide
B.8. 4-nitro-3'-nitro-4'-(4-chlorophenoxy)carbanilide
B.9. 4-nitro-3'-methyl-4'-(4-chlorophenoxy)carbanilide
B.10. 4-nitro-2'-nitro-4'-(4-chlorophenoxy)carbanilide
B.11. 4-nitro-4'-(2,4-dinitrophenoxy)carbanilide
B.12. 4-nitro-3'-chloro-4'-(2-tert-butyl-4-chlorophenoxy)carbanilide
B.13. 4-nitro-4'-(2-methyl-4-chlorophenoxy)carbanilide
B.14. 4-nitro-3'-bromo-4'-(4-bromophenoxy)carbanilide
B.15. 4-nitro-3'-bromo-4'-(4-chlorophenoxy)carbanilide
B.16. 4-nitro-3'-chloro-4'-(4-bromophenoxy)carbanilide
B.17. 3,3',4'-trichloro-4-(4-chlorophenoxy)carbanilide
B.18. 3,4'-dichloro-4-(4-chlorophenoxy)carbanilide
B.19. 3,4-dichloro-4'-(4-chlorophenoxy)carbanilide
B.20. 2-methyl-4-nitro-3'-chloro-4'-(4-chlorophenoxy)carbanilide A third group of carbanilides to be employed in the present combination is the group of carbanilides described by German Pat. No. 2,334,355. These compounds include the following:

C. Carbanilides of German Pat. No. 2,334,355

C.1. 3,3',5'-tris(trifluoromethyl)-4-methoxycarbanilide
C.2. 3-(trifluoromethoxy)-3',5'-bis(trifluoromethyl)carbanilide
C.3. 4-(trifluoromethoxy)-3',5'-bis(trifluoromethyl)carbanilide
C.4. 2,3',5'-tris(trifluoromethyl)-4-(trifluoromethoxy)carbanilide
C.5. 4-(methylthio)-3',5'-bis(trifluoromethyl)carbanilide
C.6. 4-(methylthio)-3',5'-bis(trifluoromethyl)thiocarbanilide
C.7. 3-chloro-4-(methylthio)-3',5'-bis(trifluoromethyl)carbanilide
C.8. 3-(trifluoromethylthio)-3',5'-bis(trifluoromethyl)carbanilide
C.9. 4-(trifluoromethylthio)-3',5'-bis(trifluoromethyl)carbanilide
C.10. 2-chloro-4-(trifluoromethylthio)-3',5'-bis(trifluoromethyl)carbanilide
C.11. 4-(trifluoromethylthio)-3'-(trifluoromethyl)-5'-nitrocarbanilide
C.12. 4-(trifluoromethylthio)-2',5'-bis(trifluoromethyl)-4'-nitrocarbanilide
C.13. 4,4'-bis(trifluoromethylthio)carbanilide
C.14. 4-(trifluoromethylthio)-4'-(chloromethylsulfonyl)carbanilide
C.15. 3-(difluoromethylthio)-3',5'-bis(trifluoromethyl)carbanilide
C.16. 4-(ethylthio)-3',5'-bis(trifluoromethyl)carbanilide
C.17. 3-chloro-4-(ethylthio-3',5'-bis(trifluoromethyl)carbanilide
C.18. 4-ethoxy-3,3',5'-tris(trifluoromethyl)carbanilide
C.19. 3-(trifluoromethyl)-4-ethoxy-4'-(trifluoromethylthio)carbanilide
C.20. 3-(trifluoromethyl)-4-ethoxy-3'-(trifluoromethylthio)carbanilide
C.21. 4-methyl-3-(2-chloroethoxy)-3',5'-bis(trifluoromethyl)carbanilide
C.22. 4-(1,2-dichlorovinyloxy)-3'-(trifluoromethyl)-4'-chlorocarbanilide
C.23. 4-(1,2-dichlorovinyloxy)-3',5'-bis(trifluoromethyl)carbanilide
C.24. 4-(2,2,2-trichloro-1,1-difluoroethoxy)-3',5'-bis(trifluoromethyl)carbanilide
C.25. 2-(2,2-dichloro-1,1-difluoroethoxy)-3',5'-bis(trifluoromethyl)carbanilide
C.26. 3-(2,2-dichloro-1,1-difluoroethoxy)-3',5'-bis(trifluoromethyl)carbanilide
C.27. 3-(2,2-dichloro-1,1-difluoroethoxy)-4-bromo-3',5'-bis(trifluoromethyl)carbanilide
C.28. 4-(2,2-dichloro-1,1-difluoroethoxy)-3',5'-bis(trifluoromethyl)carbanilide
C.29. 4-(2,2-dichloro-1,1-difluoroethoxy)-3'-(trifluoromethyl)-4'-chlorocarbanilide
C.30. 3-methoxy-4-(2,2-dichloro-1,1-difluoroethoxy)-3',5'-bis(trifluoromethyl)carbanilide
C.31. 3-methyl-4-(2,2-dichloro-1,1-difluoroethoxy)-3',5'-bis(trifluoromethyl)carbanilide
C.32. 3-methyl-4-(2,2-dichloro-1,1-difluoroethoxy)-4'-isopropylcarbanilide
C.33. 3-nitro-4-(2,2-dichloro-1,1-difluoroethoxy)-3',5'-bis(trifluoromethyl)carbanilide
C.34. 2-(2-chloro-1,1,2-trifluoroethoxy)-3',5'-bis(trifluoromethyl)carbanilide
C.35. 4-(2,2-dichloro-1,1-difluoroethoxy)-3,3',5'-tris(trifluoromethyl)carbanilide C.36. 3-(2-chloro-1,1,2-trifluoroethoxy)-3',5'-bis(trifluoromethyl)carbanilide
C.37. 4-(2-chloro-1,1,2-trifluoroethoxy)-3',5'-bis(trifluoromethyl)carbanilide
C.38. 4-(2-chloro-1,1,2-trifluoroethoxy)-3',5'-bis(trifluoromethyl)thiocarbanilide
C.39. 4-(2-chloro-1,1,2-trifluoroethoxy)-3'-(trifluoromethyl)-5'-nitrocarbanilide
C.40. 4,4'-bis(2-chloro-1,1,2-trifluoroethoxy)carbanilide
C.41. 4-(2-chloro-1,1,2-trifluoroethoxy)-4'-(trifluoromethylthio)carbanilide
C.42. 4-(2-chloro-1,1,2-trifluoroethoxy)-3'-(trifluoromethyl)-4'-chlorocarbanilide
C.43. 4-(2-chloro-1,1,2-trifluoroethoxy)-3,3'-bis(trifluoromethyl)-5'-nitrocarbanilide
C.44. 4-(2-chloro-1,1,2-trifluoroethoxy)-3,3',5'-tris(trifluoromethyl)carbanilide
C.45. 3-(1,1,2-trifluoroethoxy)-3',5'-bis(trifluoromethyl)carbanilide
C.46. 3-(1,1,2,2-tetrafluoroethoxy)-3',5'-bis(trifluoromethyl)carbanilide
C.47. 3-methyl-4-(1,1,2,2-tetrafluoroethoxy)-3'-(chlorodifluoromethyl)carbanilide
C.48. 3-methyl-4-(1,1,2,2-tetrafluoroethoxy)-3'-(trifluoromethyl)-4'-chlorocarbanilide
C.49. 3-(trifluoromethyl)-4-(1,1,2,2-tetrafluoroethoxy)-4'-bromocarbanilide
C.50. 3-(1,1,2,3,3,3-hexafluoro-n-propoxy)-3',5'-bis(trifluoromethyl)carbanilide
C.51. 4-(1,1,2,3,3,3-hexafluoro-n-propoxy)-3',5'-bis(trifluoromethyl)carbanilide
C.52. 3-chloro-4-(1,1,2,3,3,3-hexafluoro-n-propoxy)-3',5'-bis(trifluoromethyl)carbanilide
C.53. 3-methyl-4-(1,1,2,3,3,3-hexafluoro-n-propoxy)-3',5'-bis(trifluoromethyl)carbanilide
C.54. 4-(1,1,2,3,3,3-hexafluoro-n-propoxy)-3,3',5'-tris(trifluoromethyl)carbanilide
C.55. 4-(1,1,2,3,3,3-hexafluoro-n-propoxy)-3,3'-bis(trifluoromethyl)-5'-nitrocarbanilide
C.56. 4-(methoxycarbonylthio)-3',5'-bis(trifluoromethyl)carbanilide
C.57. 4-(4-chlorophenoxy)-4'-(trifluoromethylthio)thiocarbanilide
C.58. 4-(4-chlorophenoxy)-3',5'-bis(trifluoromethyl)carbanilide
C.59. 3-chloro-4-(4-chlorophenoxy)-3',5'-bis(trifluoromethyl)carbanilide
C.60. 4-(4-chlorophenoxy)-3'-(trifluoromethyl)-5'-nitrocarbanilide
C.61. 4-(3,5-bis(trifluoromethyl)phenoxy-3',5'-bis(trifluoromethyl)carbanilide
C.62. 4-(4-methylphenoxycarbonyl)-3',5'-bis(trifluoromethyl)carbanilide
C.63. 4-(4-methylphenoxycarbonyl)-4'-(trifluoromethylthio)carbanilide
C.64. 3,5-bis(trifluoromethyl)-2',4',6'-trichlorocarbanilide
C.65. 3,5-bis(trifluoromethyl)-2',4',5'-trichlorocarbanilide
C.66. 3,3'-bis(trifluoromethyl)-5'-nitrocarbanilide
C.67. 3,3',5-tris(trifluoromethyl)-5'-nitrocarbanilide
C.68. 2',3,5,6'-tetrakis(trifluoromethyl)-4'-nitrocarbanilide
C.69. 3-(chlorodifluoromethyl)-3',5'-bis(trifluoromethyl)carbanilide
C.70. 3-(1,1,2,2-tetrafluoroethyl)-3',5'-bis(trifluoromethyl)carbanilide
C.71. 4-phenyl-3',5'-bis(trifluoromethyl)carbanilide
C.72. 3-(fluorosulfonyl)-3',5'-bis(trifluoromethyl)carbanilide
C.73. 4-(fluorosulfonyl)-4'-(trifluoromethylthio)carbanilide
C.74. 4-(fluorosulfonyl)-3'-(trifluoromethyl)-5'-nitrocarbanilide
C.75. 4-(chloromethylsulfonyl)-3',5'-bis(trifluoromethyl)carbanilide
C.76. 2-(ethylsulfonyl)-3',5,5'-tris(trifluoromethyl)carbanilide
C.77. 2-(ethylsulfonyl)-3',5-bis(trifluoromethyl)-5'-nitrocarbanilide
C.78. 4-(trifluoromethylsulfonyl)-3',5'-bis(trifluoromethyl)carbanilide
C.79. 4-(trifluoromethylsulfonyl)-3'-(trifluoromethyl)-4'-methoxycarbanilide
C.80. 4-(trifluoromethylsulfonyl)-4'-(trifluoromethylthio)carbanilide
C.81. 4-(4-nitrophenylsulfonyl)-4'-(trifluoromethylthio)carbanilide
C.82. 4-(4-acetamidophenylsulfonyl)-4'-(trifluoromethylthio)carbanilide
C.83. 4-(4-(isopropylideneamino)phenylsulfonyl)-4'-(trifluoromethylthio)carbanilide
C.84. 4,4-sulfonylbis(3'-(trifluoromethylthio)carbanilide)
C.85. 4,4-sulfonylbis(4'-(1,2-dichlorovinyloxy)carbanilide)
C.86. 4,4-sulfonylbis(3'-(1,1,2,2-tetrafluoroethoxy)carbanilide)
C.87. 4,4-sulfonylbis(4'-(2-chloro-1,1,2-trifluoroethoxy)carbanilide)
C.88. 4,4-sulfonylbis(4'-(trifluoromethylthio)carbanilide)

All of the carbanilides to be employed in accordance with the present invention are prepared in classic synthetic procedures, such as those exemplified by U.S. Pat. No. 3,284,433 and German Pat. No. 2,334,355.

The following examples illustrate the synthesis of the carbanilides.

EXAMPLE 1

2-Amino-3-nitro-5-(trifluoromethyl)-2',4'-dimethylcarbanilide

3-Nitro-5-(trifluoromethyl)-o-phenylenediamine (2.2 grams; 0.01 mole) and 2,4-dimethylphenyl isocyanate (1.5 grams; 0.01 mole) were taken up in 40 ml. of methylene chloride, and 1 ml. of pyridine was added. The reaction mixture was maintained at 23° C. for 16 hours. The yellow precipitate was filtered and dried, m.p., >300° C. Elemental analysis showed the following:
Calculated for $C_{16}H_{15}F_3N_4O_3$: C, 52.17; H, 4.08; N, 15.22. Found: C,53.01; H, 4.05; N, 16.44.

Additional carbanilides were prepared in essentially the same procedures as Example 1.

EXAMPLE 2

2-Amino-3,3'-dinitro-5-(trifluoromethyl)-4'-chlorocarbanilide was prepared by reacting 3-nitro-5-(trifluoromethyl)-o-phenylenediamine (2.2 grams; 0.01 mole) and 3-nitro-4-chlorophenyl isocyanate (2.0 grams; 0.01 mole). The product, 3.3 grams, melted at 214°–216° C. Elemental analysis showed the following:
Calculated for $C_{14}H_9ClF_3N_5O_5$: C, 40.06; H, 2.16; N, 16.96. Found: C, 40.33; H, 1.88; N, 16.45.

EXAMPLE 3

2-Amino-3-nitro-5-(trifluoromethyl)-2',4',5'-trichlorocarbanilide was prepared by reacting 3-nitro-5-(trifluoromethyl)-o-phenylenediamine (2.2 grams; 0.1 mole) and 2,4,5-trichlorophenyl isocyanate (2.2 grams; 0.01 mole). The product melted at 225°–227° C. Elemental analysis showed the following:

Calculated for $C_{14}H_8Cl_3F_3N_4O_3$: C, 37.91; H, 1.82; N, 12.63. Found: C, 37.83; H, 1.55; N, 12.40.

EXAMPLE 4

2-Amino-3-nitro-5-(trifluoromethyl)-2'-(ethoxycarbonyl)carbanilide was prepared by reacting 3-nitro-5-(trifluoromethyl)-o-phenylenediamine (1.1 grams; 0.005 mole) and 2-(ethoxycarbonyl)phenyl isocyanate (1.0 grams; 0.005 mole). The product, 1.4 grams, melted at 186°–188° C. Elemental analysis showed the following:

Calculated for $C_{17}H_{15}F_3N_4O_5$: C, 49.52; H, 3.67; N, 13.59. Found: C, 49.75, H, 3.59; N, 13.50.

EXAMPLE 5

2-Amino-3,5'-dinitro-5-(trifluoromethyl)-2'-fluorocarbanilide was prepared from 3-nitro-5-(trifluoromethyl)-o-phenylenediamine (1.1 grams; 0.005 mole) and 2-fluoro-5-nitrophenyl isocyanate (0.8 gram; 0.005 mole). The product, 1.2 grams, melted at 218°–220° C. Elemental analysis showed the following:

Calculated for $C_{14}H_9F_4N_5O_5$: C, 41.70; H, 2.25; N, 17.37. Found: C, 41.91; H, 1.98; N, 17.27.

EXAMPLE 6

2-Amino-3,4'-dinitro-5-(trifluoromethyl)-2'-chlorocarbanilide was prepared by reacting 3-nitro-5-(trifluoromethyl)-o-phenylenediamine (1.1 grams; 0.005 mole) and 2-chloro-4-nitrophenyl isocyanate (1.0 gram; 0.005 mole). The product, 1.2 grams, melted at 220°–222° C. Elemental analysis showed the following:

Calculated for $C_{14}H_9ClF_3N_5O_5$: C, 40.06; H, 2.16; N, 16.67. Found: C, 40.11; H, 2.11; N, 16.48.

EXAMPLE 7

2-Amino-3-nitro-3',5-bis(trifluoromethyl)-4'-chlorocarbanilide was prepared by reacting 2-amino-3-nitro-5-(trifluoromethyl)-o-phenylenediamine (2.2 grams; 0.01 mole) and 4-chloro-3-(trifluoromethyl)phenyl isocyanate (2.2 grams; 0.01 mole). The product, 1.8 grams, melted at 214°–216° C. Elemental analysis showed the following:

Calculated for $C_{15}H_9ClF_6N_4O_3$: C, 40.70; H, 2.05; N, 12.66. Found: C, 40.90; H, 2.04; N, 12.67.

EXAMPLE 8

2-Amino-3-nitro-3',5,5'-tris(trifluoromethyl)carbanilide was prepared by reacting 3-nitro-5-(trifluoromethyl)-o-phenylenediamine (1.1 grams; 0.005 mole) and (3,5-bis(trifluoromethyl)phenyl)carbamoyl chloride (1.4 grams; 0.005 mole). Elemental analysis of the product showed the following:

Calculated for $C_{16}H_9F_9N_4O_3$: C, 40.35; H, 1.92; N, 11.76. Found: C, 40.52; H, 1.82; N, 11.78.

EXAMPLE 9

2-Amino-3-nitro-2',5-bis(trifluoromethyl)-4'-chlorocarbanilide was prepared by reacting 3-nitro-5-(trifluoromethyl)-o-phenylenediamine (2.2 grams; 0.01 mole) and 4-chloro-2-(trifluoromethyl)phenyl isocyanate (2.2 grams; 0.01 mole). The product melted at 245°–247° C. Elemental analysis showed the following:

Calculated for $C_{15}H_9ClF_6N_4O_3$: C, 40.70; H, 2.05; N, 12.66. Found: C, 40.94; H, 1.88; N, 12.55.

EXAMPLE 10

2-Amino-3-nitro-5-(trifluoromethyl)-2'-methyl-4'-bromocarbanilide was prepared by reacting 3-nitro-5-(trifluoromethyl)-o-phenylenediamine (2.2 grams; 0.01 mole) and 2-methyl-4-bromophenyl isocyanate (2.1 grams; 0.01 mole). The product melted at 230°–231° C. Elemental analysis showed the following:

Calculated for $C_{15}H_{11}BrF_3N_4O_3$: C, 41.59; H, 2.79; N, 12.93. Found: C, 41.40; H, 2.65; N, 12.71.

EXAMPLE 11

2-Amino-3-nitro-5-(trifluoromethyl)-2',6'-dibromo-4'-fluorocarbanilide was prepared by reacting 3-nitro-5-(trifluoromethyl)-o-phenylenediamine (2.2 grams; 0.01 mole) and 2,6-dibromo-4-fluorophenyl isocyanate. The product melted at 249°–251° C. Elemental analysis showed the following:

Calculated for $C_{14}H_8Br_2F_4N_4O_3$: C, 32.59; H, 1.56; N, 10.86. Found: C, 32.64; H, 1.39; N, 10.76.

The methods and compositions of the present invention can be used with all species of poultry. Because of their economic importance, chickens and turkeys are the principal species requiring anticoccidial treatment. However, the present invention can be practiced with other poultry, such as ducks, geese, pheasants, and quail.

The present invention is practiced in the usual manner of anticoccidials. Since coccidiosis affects the intestinal tract, the compositions of the present invention are those which are suited for oral administration. The polyether antibiotics are generally of low solubility in water, even in the sodium or other salt form. Therefore, the present invention is preferably practiced by administering the subject combinations in a feedstuff rather than in drinking water. Furthermore, it is the practice of the industry to supply poultry with only one source of feed, constituting the entire food supply of the poultry. Therefore, in a preferred practice of the present invention, the anticoccidial combinations are supplied in a total feed, with concentrations adjusted accordingly. Those skilled in the art, however, will recognize that concentrations are to be adjusted upward, should it be desired to supply poultry with multiple sources of food only one of which contains the combinations of the present invention.

The components of the present combinations can be employed in a wide range of concentrations in the feed administered to poultry. In general, for those components which are known anticoccidials, the maxima to be employed in accordance with the present invention are the same as the maxima for anticoccidial treatment by the individual components. The lower limits in accordance with the present invention are generally less than for therapy by the individual components, especially where the components are being used to minimize side effects of either individual component.

Representative amounts of selected polyether antibiotics are as follows:

from about 20 to about 120 ppm of monensin;
from about 25 to about 100 ppm of narasin;
from about 35 to about 125 ppm of lasalocid;
from about 25 to about 100 ppm of salinomycin;
from about 5 to about 15 ppm of A-204;

from about 25 to about 100 ppm of Ionomycin.
from about 25 to about 100 ppm of X-206;
from about 50 to about 200 ppm of nigericin; and
from about 10 to about 50 ppm of dianemycin.

The carbanilide is generally employed in a concentration of from about 10 to about 250 ppm, preferably from about 50 to about 100 ppm. Amounts will be adjusted downward where more than one polyether, or more than one carbanilide, is employed.

Since the polyether antibiotics, alone, are active as anticoccidials, the present combinations are useful regardless of the exact concentration of the carbanilide. As noted above, certain of the carbanilides, alone, exhibit anticoccidial activity. Therefore, preferred embodiments of the present invention are those wherein the carbanilide is employed in a concentration that potentiates the anticoccidial activity of the polyether (where the carbanilide is, itself, lacking anticoccidial activity); or in a concentration that is synergistic with the anticoccidial activity of the polyether (where the carbanilide also exhibits anticoccidial activity).

The Group A compounds include both compounds exhibiting no independent anticoccidial activity, at typical rates, as well as compounds exhibiting independent anticoccidial activity. Each of the Group A compounds has been found to potentiate or synergize, respectively, the activity of a representative polyether antibiotic, monensin. The potentiating and synergizing effect of the Group A compounds is shown in Tables I and IV, below.

The Group B compounds are taught in 3,284,433 to exhibit anticoccidial activity. Therefore, they are preferably employed in amounts which are synergistic as to the anticoccidial activity of the polyethers.

The Group C compounds are taught in German Pat. No. 2,334,355 to exhibit anticoccidial activity. They are likewise preferably employed in amounts which are synergistic as to the anticoccidial activity of the polyethers. Data on the effects of the Group C compounds is shown in Tables I, II, and III, below. As will be noted, not all Group C compounds are synergistic in the specific rates and against the specific Eimeria organisms reported below. Compounds C.13., C.58., C.65., and C.86. are regarded as synergistic, whereas compounds C.1., C.5., C.6., C.8., C.11., C.62., and C.76. are regarded as not synergistic in the tests reported below. However, simple range-finding experiments as to any of the carbanilides to be employed in the present invention will enable those skilled in the art to determine the preferred potentiating or synergistic amounts of the respective carbanilide.

Poultry feedstuffs of all types and formulae in the poultry industry may be used in administering the combinations of the present invention. The following formulae are exemplary only.

| Ingredients | Percent |
|---|---|
| Broiler Starter | |
| Corn, Yellow, Ground | 50.0 |
| Soybean Oil Meal, Solvent Extracted Dehulled (50%) | 30.9 |
| Animal Fat | 6.5 |
| Fish Meal with Solubles (60%) | 5.0 |
| Corn Distillers Dried Solubles | 4.0 |
| Dicalcium Phosphate, Feed Grade | 1.8 |
| Calcium Carbonate (Ground Limestone) | 0.8 |
| Vitamin Premix TK-01 (1.03)[1] | 0.5 |
| Salt (NaCl) | 0.3 |
| Trace Mineral Premix TK-01 (1.02)[2] | 0.1 |
| Methionine Hydroxy Analog | 0.1 |
| Total | 100.0 |
| Broiler Grower | |
| Corn, Yellow, Ground | 57.7 |
| Soybean Meal, Solvent, Extracted, Dehulled (50%) | 31.7 |
| Animal Fat (Beef tallow) | 6.0 |
| Dicalcium Phosphate, Feed Grade | 2.7 |
| Calcium Carbonate (Ground Limestone) | 0.9 |
| Vitamin Premix TK-01 (1.03)[1] | 0.5 |
| Salt (NaCl) | 0.2 |
| Methionine Hydroxy Analog | 0.2 |
| Trace Mineral Premix TK-01 (1.02)[2] | 0.1 |
| Total | 100.0 |
| Chick Starter, Light Breeds | |
| Corn, Yellow, Ground | 56.3 |
| Soybean Meal, Solvent Extracted, Dehulled (50%) | 17.9 |
| Wheat Middlings | 10.0 |
| Corn Distillers Dried Solubles | 5.0 |
| Fish Meal with Solubles | 5.0 |
| Alfalfa Meal, Dehydrated (17%) | 2.5 |
| Dicalcium Phosphate, Feed Grade | 1.3 |
| Calcium Carbonate | 0.9 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |
| Pullet Grower | |
| Corn, Yellow, Ground | 73.5 |
| Soybean Meal, Solvent Extracted, Dehulled (50%) | 21.9 |
| Dicalcium Phosphate, Feed Grade | 2.5 |
| Calcium Carbonate | 1.0 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |
| Pullet Developer | |
| Corn, Yellow, Ground | 67.5 |
| Oats, Ground Whole | 15.0 |
| Soybean Meal, Solvent Extracted, Dehulled (50%) | 13.4 |
| Dicalcium Phosphate, Feed Grade | 2.1 |
| Calcium Carbonate | 1.0 |
| Vitamin Premix[1] | 0.5 |
| Methionine Hydroxy Analog | 0.3 |
| Salt (NaCl) | 0.2 |
| Trace Mineral Premix[2] | 0.1 |
| Total | 100.0 |
| Turkey Starter | |
| Soybean Meal, Solvent Extracted, Dehulled | 40.7 |
| Corn, Yellow, Ground | 39.7 |
| Fish Meal with Solubles | 5.0 |
| Beef Tallow | 5.0 |
| Corn Distillers Dried Solubles | 2.5 |
| Alfalfa Meal, Dehydrated (17%) | 2.5 |
| Dicalcium Phosphate, Feed Grade | 2.5 |
| Calcium Carbonate | 1.2 |
| Vitamin Premix[1] | 0.5 |
| Salt (NaCl) | 0.2 |

-continued

| Ingredients | Percent |
|---|---|
| Trace Mineral Premix[2] | 0.1 |
| Methionine Hydroxy Analog | 0.1 |
| Total | 100.0 |
| Turkey Finisher | |
| Corn, Yellow, Ground | 71.2 |
| Soybean Meal, Solvent Extracted, Dehulled (50%) | 9.9 |
| Corn Distillers Dried Solubles | 5.0 |
| Alfalfa Meal, Dehydrated (17%) | 5.0 |
| Animal Fat | 3.0 |
| Fish Meal With Solubles | 2.5 |
| Dicalcium Phosphate, Feed Grade | 1.7 |
| Calcium Carbonate | 0.5 |
| Vitamin Premix[1] | 0.5 |
| Salt (NaCl) | 0.4 |
| Methionine Hydroxy Analog | 0.2 |
| Trace Mineral Premix[2] | 0.1 |
| Total | 100.0 |

[1]/Vitamin premix provides 3000 IU of vitamin A, 900 ICU of vitamin D, 40 mg. of vitamin E, 0.7 mg. of vitamin K, 1000 mg. of choline, 70 mg. of niacin, 4 mg. of pantothenic acid, 4 mg. of riboflavin, 0.10 mg. of vitamin $B_{12}$, 0.10 mg. of biotin and 125 mg. of ethoxyquin per kg. of complete feed.
[2]/Trace mineral premix provides 75 mg. of manganese, 50 mg. of zinc, 25 mg. of iron and 1 mg. of iodine per kg. of complete feed.

The foregoing compositions are typical of feedstuffs actually administered to poultry. Premixes are commonly used in the poultry industry, and the combinations of the present invention can also be formulated as premixes. Such premixes typically comprise the polyether antibiotic, the selected carbanilide, and a solid substance acceptable as a feedstuff, such as corn meal, rice hulls, crushed limestone, soybean meal, soya grits, distiller's dried grains, citrus meal, wheat middlings, clays and the like. Such a premix is mixed or blended with other substances to constitute either an intermediate premix or the finished feed.

A representative premix in accordance with the present invention is as follows:
monensin: 45 grams activity,
a selected carbanilide in accordance with the present invention: 45 grams,
rice hulls q.s. ad 454 grams, This formulation is mixed thoroughly and can be added to one ton of finished feed to supply suitable amounts of the components in accordance with the present invention.

The present invention was evaluated in chickens as follows: one-week-old broiler chicks were fed a medicated or control ration, typically for one day, prior to infection (by gavage) with oocysts of a coccidiosis-causing organism, generally 750,000 oocysts of *Eimeria acervulina* and 75,000 oocysts of *Eimeria tenella*. The chicks were maintained on their respective rations for an additional period of time, typically six days. There were five chicks in a group and generally two replicates per treatment. Anticoccidial efficacy was determined by lesion scores. To determine lesion scores, the birds were sacrificed and the severity of lesions scored on a 0–4 scale, with lesion-free birds scored as 0, extremely severe infections scored as 4, and intermediate degrees of infection scored as 1, 2, or 3. The scores of all birds which received a given treatment were averaged.

Most of the compounds were tested in a preliminary test "A"; in this test, monensin was tested alone at 50 ppm and the carbanilide compound was tested in combination with monensin, each at 50 ppm. In a secondary test "B", monensin and the carbanilide compound were each tested alone, at 50 ppm, and the two were tested in combination, each at 50 ppm. Additional tests at more varied concentrations were also conducted with certain of the compounds.

The results are reported in the following tables. The concentration of monensin and the carbanilides is expressed as the parts per million (ppm) of the total feed provided to the chicks.

TABLE I

| Compound Number | | | LESION SCORES | | | |
|---|---|---|---|---|---|---|
| | | | Eimeria acervulina monensin | | Eimeria tenella monensin | |
| | | | 0 | 50 | 0 | 50 |
| A.3. | A | 0 | 2.8 | 1.6 | 2.0 | 1.9 |
| | | 50 | | 0.7 | | 0.9 |
| | B | 0 | 3.0 | 1.2 | 2.0 | 1.2 |
| | | 50 | 3.0 | 1.2 | 2.5 | 0.7 |
| A.4. | A | 0 | 2.8 | 1.6 | 2.0 | 0.9 |
| | | 50 | | 0 | | 0 |
| | B | 0 | 3.0 | 1.2 | 2.0 | 1.2 |
| | | 50 | 3.0 | 0.9 | 2.4 | 0.6 |
| A.5. | A | 0 | 2.4 | 1.2 | 2.5 | 1.4 |
| | | 50 | | 0.3 | | 0.4 |
| | B | 0 | 3.0 | 1.2 | 2.0 | 1.2 |
| | | 50 | 3.0 | 1.1 | 2.2 | 0 |
| A.6. | A | 0 | 2.8 | 1.6 | 2.0 | 0.9 |
| | | 50 | | 1.6 | | 0.6 |
| | B | 0 | 3.0 | 1.2 | 2.0 | 1.2 |
| | | 50 | 2.9 | 0.8 | 2.5 | 0.5 |
| A.7. | A | 0 | 2.5 | 1.6 | 2.4 | 2.3 |
| | | 50 | | 0.9 | | 0.4 |
| | B | 0 | 3.0 | 1.2 | 2.0 | 1.2 |
| | | 50 | 3.0 | 1.4 | 1.8 | 0.6 |
| A.8. | A | 0 | 3.0 | 1.2 | 2.1 | 0.9 |
| | | 50 | | 0.4 | | 0.2 |
| | B | 0 | 3.3 | 1.3 | 3.0 | 2.2 |
| | | 50 | 2.6 | 0.8 | 3.0 | 1.0 |
| A.9. | A | 0 | 3.0 | 1.2 | 2.1 | 0.9 |
| | | 50 | | 0.7 | | 0.9 |
| | B | 0 | 3.3 | 1.3 | 3.0 | 2.2 |
| | | 50 | 2.8 | 0.8 | 2.9 | 1.3 |
| A.10. | A | 0 | 2.7 | 1.7 | 3.0 | 1.0 |
| | | 50 | | 0.5 | | 0.6 |
| | B | 0 | 3.3 | 1.3 | 3.0 | 2.2 |
| | | 50 | 2.4 | 0.9 | 2.7 | 1.7 |
| A.11. | A | 0 | 3.6 | 1.2 | 3.0 | 1.2 |
| | | 50 | | 0.6 | | 0.8 |
| | B | 0 | 3.3 | 1.3 | 3.0 | 2.2 |
| | | 50 | 2.6 | 1.4 | 2.8 | 1.1 |
| A.12. | A | 0 | 2.8 | 1.1 | 2.3 | 1.0 |
| | | 50 | | 1.1 | | 0.6 |
| | B | 0 | 3.3 | 1.3 | 3.0 | 2.2 |
| | | 50 | 2.5 | 0.9 | 2.9 | 0.8 |
| A.13. | A | 0 | 3.0 | 1.2 | 2.1 | 0.9 |
| | | 50 | | 0.9 | | 0.5 |
| | B | 0 | 3.3 | 1.3 | 3.0 | 2.2 |
| | | 50 | 2.9 | 1.4 | 3.0 | 1.2 |
| A.14. | A | 0 | 1.2 | 2.1 | 0.9 | |
| | | 3.0 | | | | |
| | | 50 | | 1.2 | | 0.6 |
| | B | 0 | 3.3 | 1.3 | 3.0 | 2.2 |
| | | 50 | 2.6 | 1.1 | 3.0 | 1.0 |
| C.8. | A | 0 | 2.7 | 1.7 | 3.0 | 1.0 |
| | | 50 | | 1.2 | | 0.4 |
| | B | 0 | 3.3 | 1.3 | 3.0 | 2.2 |
| | | 50 | 2.3 | 1.1 | 3.0 | 0.3 |
| A.15. | A | 0 | 3.2 | 1.5 | 2.4 | 1.9 |
| | | 50 | | 1.8 | | 1.0 |
| | B | 0 | 3.3 | 1.3 | 3.0 | 2.2 |
| | | 50 | 2.6 | 1.6 | 2.6 | 1.1 |
| A.16. | A | 0 | 3.0 | 1.1 | 2.6 | 1.0 |
| | | 50 | | 0.9 | | 0.5 |
| | B | 0 | 3.3 | 1.3 | 3.0 | 2.2 |
| | | 50 | 2.8 | 1.0 | 2.8 | 1.1 |
| A.17. | A | 0 | 2.8 | 1.4 | 2.6 | 0.8 |
| | | 50 | | 0.9 | | 0.9 |
| | B | 0 | 2.6 | 1.0 | 2.5 | 1.5 |
| | | 50 | 2.4 | 0.6 | 2.6 | 1.3 |
| A.18. | A | 0 | 2.8 | 1.4 | 2.6 | 0.8 |
| | | 50 | | 0.1 | | 0.3 |

TABLE I-continued

| Compound Number | | | Eimeria acervulina monensin | | Eimeria tenella monensin | |
|---|---|---|---|---|---|---|
| | | | 0 | 50 | 0 | 50 |
| | B | 0 | 2.6 | 1.0 | 2.5 | 1.5 |
| | | 50 | 2.7 | 0.6 | 2.0 | 0.7 |
| A.19. | A | 0 | 2.8 | 1.4 | 2.6 | 0.8 |
| | | 50 | | 0.4 | | 0.4 |
| | B | 0 | 2.6 | 1.0 | 2.5 | 1.5 |
| | | 50 | 2.7 | 0.4 | 2.4 | 0.7 |
| A.20. | A | 0 | 2.8 | 1.4 | 2.6 | 0.8 |
| | | 50 | | 0.5 | | 0.8 |
| | B | 0 | 2.6 | 1.0 | 2.5 | 1.5 |
| | | 50 | 2.4 | 0.4 | 1.4 | 0.1 |
| A.21. | A | 0 | 2.5 | 0.9 | 2.4 | 1.7 |
| | | 50 | | 1.3 | | 1.0 |
| | B | 0 | 2.6 | 1.0 | 2.5 | 1.5 |
| | | 50 | 2.3 | 1.0 | 2.2 | 0.7 |
| A.22. | A | 0 | 3.2 | 2.3 | 3.0 | 1.8 |
| | | 50 | | 1.3 | | 0.8 |
| | B | 0 | 2.6 | 1.0 | 2.5 | 1.5 |
| | | 50 | 2.7 | 1.3 | 2.2 | 0.6 |
| A.23. | A | 0 | 2.6 | 0.6 | 2.7 | 0.9 |
| | | 50 | | 0.5 | | 0.6 |
| | B | 0 | 2.6 | 1.0 | 2.5 | 1.5 |
| | | 50 | 2.8 | 0.6 | 2.0 | 0.4 |
| A.24. | A | 0 | 2.5 | 0.9 | 2.4 | 1.7 |
| | | 50 | | 0.9 | | 0.6 |
| | B | 0 | 2.6 | 1.0 | 2.5 | 1.5 |
| | | 50 | 2.8 | 0.8 | 2.2 | 0.7 |
| A.25. | A | 0 | 2.7 | 0.6 | 2.7 | 0.9 |
| | | 50 | | 1.1 | | 0.3 |
| | B | 0 | 2.6 | 1.0 | 2.5 | 1.5 |
| | | 50 | 2.9 | 0.9 | 1.8 | 0.6 |
| A.26. | A | 0 | 2.6 | 0.6 | 2.7 | 0.9 |
| | | 50 | | 0.7 | | 0.4 |
| | B | 0 | 2.6 | 1.0 | 2.5 | 1.5 |
| | | 50 | 2.8 | 1.3 | 2.3 | 0.8 |
| A.27. | A | 0 | 2.6 | 0.6 | 2.7 | 0.9 |
| | | 50 | | 0.3 | | 0.7 |
| | B | 0 | 2.6 | 1.2 | 2.6 | 1.5 |
| | | 50 | 2.8 | 0.9 | 2.6 | 1.2 |
| A.28. | A | 0 | 2.6 | 0.6 | 2.7 | 0.9 |
| | | 50 | | 0.4 | | 0.9 |
| | B | 0 | 2.6 | 1.2 | 2.6 | 1.5 |
| | | 50 | 2.7 | 0.8 | 2.2 | 0.7 |
| A.29. | A | 0 | 2.6 | 0.6 | 2.7 | 0.9 |
| | | 50 | | 0.8 | | 0.4 |
| | B | 0 | 2.6 | 1.2 | 2.6 | 1.5 |
| | | 50 | 1.7 | 1.4 | 1.2 | 0.6 |
| A.30. | A | 0 | 2.5 | 0.9 | 2.4 | 1.7 |
| | | 50 | | 0.8 | | 0.4 |
| | B | 0 | 2.6 | 1.2 | 2.6 | 1.5 |
| | | 50 | 2.9 | 0.2 | 2.0 | 0.2 |
| A.31. | A | 0 | 2.7 | 1.6 | 2.5 | 1.6 |
| | | 50 | | 0.3 | | 0.7 |
| | B | 0 | 2.6 | 1.2 | 2.6 | 1.5 |
| | | 50 | 2.8 | 0.8 | 2.7 | 1.2 |
| | B | 0 | 2.4 | 1.2 | 2.2 | 1.8 |
| | | 50 | 2.7 | 0.9 | 3.0 | 1.6 |
| A.32. | A | 0 | 2.7 | 1.6 | 2.5 | 1.6 |
| | | 50 | | 0.4 | | 0.6 |
| | B | 0 | 2.6 | 1.2 | 2.6 | 1.5 |
| | | 50 | 2.8 | 0.7 | 2.1 | 0.9 |
| | B | 0 | 2.4 | 1.2 | 2.2 | 1.8 |
| | | 50 | 2.5 | 1.0 | 2.9 | 1.0 |
| A.33. | B | 0 | 2.8 | 1.2 | 2.7 | 1.6 |
| | | 50 | 2.8 | 0.5 | 2.6 | 1.0 |
| A.34. | B | 0 | 2.8 | 1.2 | 2.7 | 1.6 |
| | | 50 | 2.9 | 0.3 | 2.2 | 0.3 |
| A.35. | B | 0 | 2.8 | 1.2 | 2.7 | 1.6 |
| | | 50 | 2.8 | 0.2 | 3.0 | 0.9 |
| A.36. | B | 0 | 2.8 | 1.2 | 2.7 | 1.6 |
| | | 50 | 2.2 | 0 | 2.6 | 0.1 |
| A.37. | B | 0 | 2.8 | 1.2 | 2.7 | 1.6 |
| | | 50 | 2.0 | 0.4 | 2.9 | 1.2 |
| A.38. | B | 0 | 2.8 | 1.2 | 2.7 | 1.6 |
| | | 50 | 2.6 | 0.4 | 2.9 | 1.3 |
| A.39. | A | 0 | 3.6 | 1.6 | 2.8 | 1.2 |
| | | 50 | | 1.4 | | 0.5 |
| | B | 0 | 3.6 | 2.0 | 2.9 | 1.3 |
| | | 50 | 3.1 | 0.5 | 3.0 | 0.8 |
| A.40. | A | 0 | 3.6 | 1.6 | 2.8 | 1.2 |
| | | 50 | | 1.3 | | 0.3 |
| | B | 0 | 3.6 | 2.0 | 2.9 | 1.3 |
| | | 50 | 2.6 | 0.8 | 2.6 | 0.8 |
| A.41. | A | 0 | 3.6 | 1.6 | 2.8 | 1.2 |
| | | 50 | | 1.3 | | 0.2 |
| | B | 0 | 3.6 | 2.0 | 2.9 | 1.3 |
| | | 50 | 2.1 | 0 | 2.2 | 0.4 |
| A.42. | A | 0 | 2.7 | 1.6 | 2.6 | 1.6 |
| | | 50 | | 0.3 | | 0.7 |
| | B | 0 | 3.6 | 2.0 | 2.9 | 1.3 |
| | | 50 | 3.2 | 2.5 | 2.1 | 0 |
| A.43. | A | 0 | 2.7 | 1.6 | 2.6 | 1.6 |
| | | 50 | | 1.3 | | 0.4 |
| | B | 0 | 3.2 | 1.1 | 1.9 | 0.8 |
| | | 50 | 3.1 | 0.8 | 2.3 | 0.4 |
| A.44. | A | 0 | 3.6 | 1.6 | 2.8 | 1.2 |
| | | 50 | | 1.2 | | 0.4 |
| | B | 0 | 3.2 | 1.1 | 1.9 | 0.8 |
| | | 50 | 2.9 | 0.5 | 2.6 | 0.6 |
| A.45. | A | 0 | 3.0 | 0.9 | 2.8 | 0.5 |
| | | 50 | | 0.8 | | 0.3 |
| | B | 0 | 3.2 | 1.1 | 1.9 | 0.8 |
| | | 50 | 2.7 | 1.0 | 2.1 | 0.2 |
| A.46. | A | 0 | 3.0 | 0.7 | 2.8 | 0.2 |
| | | 50 | | 1.0 | | 0.2 |
| | B | 0 | 3.2 | 1.1 | 1.9 | 0.8 |
| | | 50 | 2.9 | 0.9 | 2.1 | 0.2 |
| A.47. | A | 0 | 2.8 | 1.0 | 3.0 | 1.2 |
| | | 50 | | 1.4 | | 0.7 |
| | B | 0 | 3.2 | 1.1 | 1.9 | 0.8 |
| | | 50 | 2.7 | 0.9 | 2.4 | 0.5 |
| A.48. | A | 0 | 2.8 | 1.0 | 3.0 | 1.2 |
| | | 50 | | 0.9 | | 0.7 |
| | B | 0 | 3.2 | 1.1 | 1.9 | 0.8 |
| | | 50 | 3.3 | 1.0 | 2.3 | 0.4 |
| A.49. | A | 0 | 3.0 | 0.7 | 2.8 | 0.2 |
| | | 50 | | 0.6 | | 0.4 |
| | B | 0 | 3.2 | 1.1 | 1.9 | 0.8 |
| | | 50 | 3.1 | 0.3 | 2.8 | 0.2 |
| A.50. | B | 0 | 2.8 | 1.0 | 1.7 | 0.5 |
| | | 50 | 3.0 | 0 | 2.0 | 0 |
| A.51. | B | 0 | 2.8 | 1.0 | 1.7 | 0.5 |
| | | 50 | 1.3 | 0 | 1.1 | 0 |
| A.52. | B | 0 | 2.8 | 1.0 | 1.7 | 0.5 |
| | | 50 | 2.8 | 0 | 2.1 | 0.2 |
| A.53. | A | 0 | 2.7 | 1.6 | 2.5 | 1.6 |
| | | 50 | | 0.8 | | 0.9 |

TABLE I-continued

| Compound Number | | | Eimeria acervulina monensin | | Eimeria tenella monensin | |
|---|---|---|---|---|---|---|
| | | | 0 | 50 | 0 | 50 |
| | B | 0 | 2.4 | 1.2 | 2.2 | 1.8 |
| | | 50 | 2.8 | 0.8 | 2.6 | 1.4 |
| A.54. | A | 0 | 3.1 | 2.0 | 2.4 | 0.6 |
| | | 50 | | 1.7 | | 0.6 |
| | B | 0 | 2.4 | 1.2 | 2.2 | 1.8 |
| | | 50 | 2.6 | 0.7 | 2.9 | 0.4 |
| A.55. | B | 0 | 2.4 | 1.2 | 2.2 | 1.8 |
| | | 50 | 2.9 | 0.8 | 2.5 | 0.1 |
| A.56. | B | 0 | 2.4 | 1.2 | 2.2 | 1.8 |
| | | 50 | 2.8 | 0.6 | 2.8 | 0.2 |
| A.57. | A | 0 | 2.7 | 1.6 | 2.5 | 1.6 |
| | | 50 | | 0.7 | | 0.9 |
| | B | 0 | 2.4 | 1.2 | 2.2 | 1.8 |
| | | 50 | 3.0 | 1.2 | 2.8 | 0.9 |
| A.58. | A | 0 | 2.7 | 1.6 | 2.5 | 1.6 |
| | | 50 | | 0.9 | | 0.7 |
| | B | 0 | 2.4 | 1.2 | 2.2 | 1.8 |
| | | 50 | 2.7 | 0.7 | 2.7 | 0.8 |
| A.59. | A | 0 | 2.9 | 0.9 | 2.2 | 1.7 |
| | | 50 | | 0.5 | | 1.4 |
| | B | 0 | 2.4 | 1.2 | 2.2 | 1.8 |
| | | 50 | 2.9 | 0.7 | 2.9 | 1.1 |
| A.60. | A | 0 | 2.7 | 1.6 | 2.5 | 1.6 |
| | | 50 | | 0.6 | | 0.7 |
| | B | 0 | 2.7 | 1.2 | 2.1 | 1.1 |
| | | 50 | 2.9 | 0.8 | 2.7 | 1.6 |
| A.61. | A | 0 | 3.0 | 1.5 | 2.8 | 1.9 |
| | | 50 | | 0.8 | | 1.7 |
| | B | 0 | 2.0 | 0.2 | 2.8 | 1.3 |
| | | 50 | 2.0 | 0.7 | 3.1 | 2.2 |
| A.62. | B | 0 | 2.0 | 0.2 | 2.8 | 1.3 |
| | | 50 | 0.4 | 0 | 2.4 | 0.8 |
| A.63. | B | 0 | 2.0 | 0.2 | 2.8 | 1.3 |
| | | 50 | 2.6 | 0.1 | 2.9 | 0.6 |
| A.64. | B | 0 | 2.0 | 0.2 | 2.8 | 1.3 |
| | | 50 | 0.7 | 0 | 2.4 | 0.8 |

TABLE II

| COMPOUND NO. | | | LESION SCORES | | | | | | | |
|---|---|---|---|---|---|---|---|---|---|---|
| | | | Eimeria acervulina monensin | | | | | Eimeria tenella monensin | | |
| C.1. | | 0 | 50 | 100 | | | 0 | 50 | 100 | |
| | 0 | 3.1 | 1.3 | 0.2 | | | 2.0 | 0.5 | 0 | |
| | 50 | 2.8 | 0.8 | | | | 2.0 | 0.3 | | |
| | 100 | 2.1 | | | | | 2.1 | | | |
| | | 0 | 20 | 40 | 80 | 160 | 0 | 20 | 40 | 80 | 160 |
| | 0 | 2.9 | 2.6 | 1.2 | 0.4 | 0 | 2.6 | 2.9 | 2.2 | 0.6 | 0.2 |
| | 40 | 3.0 | | 2.3 | | | 2.7 | | 2.5 | | |
| | 80 | 2.7 | | | 0.2 | | 2.6 | | | 0.5 | |
| | 160 | 2.4 | | | | | 1.9 | | | | |
| C.5. | | 0 | 20 | 40 | 80 | 160 | 0 | 20 | 40 | 80 | 160 |
| | 0 | 2.9 | 2.6 | 1.2 | 0.4 | 0 | 2.6 | 2.9 | 2.2 | 0.6 | 0.2 |
| | 40 | 3.0 | | 1.0 | | | 1.4 | | 1.7 | | |
| | 80 | 2.4 | | | 0.3 | | 2.9 | | | 1.3 | |
| | 160 | 3.0 | | | | | 2.7 | | | | |
| C.6. | | 0 | 50 | 100 | | | 0 | 50 | 100 | |
| | 0 | 3.1 | 1.3 | 0.2 | | | 2.0 | 0.5 | 0 | |
| | 50 | 3.3 | 1.3 | | | | 2.0 | 0.8 | | |
| | 100 | 2.7 | | | | | 2.4 | | | |
| | | 0 | 20 | 40 | 50 | 80 | 160 | 0 | 20 | 40 | 50 | 80 | 160 |
| | 0 | 2.9 | 2.6 | 1.2 | | 0.4 | 0 | 2.6 | 2.9 | 2.2 | | 0.6 | 0.2 |
| | 100 | | | | 1.8 | | | | | | 1.6 | | |
| | 200 | 1.7 | | | | | | 2.0 | | | | | |
| C.8. | | 0 | 50 | 100 | | | 0 | 50 | 100 | |
| | 0 | 3.1 | 1.3 | 0.2 | | | 2.0 | 0.5 | 0 | |
| | 50 | | 0.7 | | | | | 0.1 | | |
| | 100 | | | | | | | | | |
| C.11. | | 0 | 50 | 100 | | | 0 | 50 | 100 | |
| | 0 | 3.1 | 1.3 | 0.2 | | | 2.0 | 0.5 | 0 | |
| | 50 | 2.6 | 0.2 | | | | 1.9 | 0 | | |
| | 100 | 0.2 | | | | | 0.2 | | | |
| C.13. | | 0 | 50 | 100 | | | 0 | 50 | 100 | |
| | 0 | 3.1 | 1.3 | 0.2 | | | 2.0 | 0.5 | 0 | |
| | 50 | 0 | 0 | | | | 0.1 | 0 | | |
| | 100 | 0 | | | | | 0.2 | | | |
| | | 0 | 20 | 40 | 80 | 160 | 0 | 20 | 40 | 80 | 160 |
| | 0 | 2.9 | 2.6 | 1.2 | 0.4 | 0 | 2.6 | 2.9 | 2.2 | 0.6 | 0.2 |
| | 10 | 2.6 | 1.8 | | | | 3.0 | 1.4 | | | |
| | 20 | 2.4 | 0.7 | | | | 2.8 | 0.7 | | | |
| | 40 | 0.8 | | | | | 1.6 | | | | |
| C.58. | | 0 | 50 | 100 | | | 0 | 50 | 100 | |
| | 0 | 3.1 | 1.3 | 0.2 | | | 2.0 | 0.5 | 0 | |
| | 50 | 2.6 | 0.1 | | | | 1.5 | 0 | | |
| | 100 | 2.8 | | | | | 0.5 | | | |
| | | 0 | 20 | 40 | 80 | 160 | 0 | 20 | 40 | 80 | 160 |
| | 0 | 2.9 | 2.6 | 1.2 | 0.4 | 0 | 2.6 | 2.9 | 2.2 | 0.6 | 0.2 |
| | 40 | | | 0.7 | | | | | 0.8 | | |
| | 80 | 2.9 | | | | | 2.2 | | | | |
| C.62. | | 0 | 50 | 100 | | | 0 | 50 | 100 | |
| | 0 | 3.1 | 1.3 | 0.2 | | | 2.0 | 0.5 | 0 | |
| | 50 | 2.9 | 1.3 | | | | 1.1 | 0.4 | | |
| | 100 | 2.9 | | | | | 1.9 | | | |
| C.65. | | 0 | 50 | 100 | | | 0 | 50 | 100 | |

TABLE II-continued

LESION SCORES

| COMPOUND NO. | Eimeria acervulina monensin | | | | | Eimeria tenella monensin | | | | |
|---|---|---|---|---|---|---|---|---|---|---|
| | 0 | 3.1 | 1.3 | 0.2 | | 2.0 | 0.5 | 0 | | |
| | 50 | 3.2 | 0.3 | | | 1.3 | 0 | | | |
| | 100 | 2.8 | | | | 0.9 | | | | |
| C.76. | 0 | 50 | 100 | | | 0 | 50 | 100 | | |
| | 0 | 3.1 | 1.3 | 0.2 | | 2.0 | 0.5 | 0 | | |
| | 50 | 3.0 | 0.8 | | | 1.9 | 0.2 | | | |
| | 100 | 3.0 | | | | 1.5 | | | | |
| | 0 | 20 | 40 | 80 | 160 | 0 | 20 | 40 | 80 | 160 |
| | 0 | 2.9 | 2.6 | 1.2 | 0.4 | 0 | 2.6 | 2.9 | 2.2 | 0.6 | 0.2 |
| | 40 | 2.1 | | 1.5 | | | 2.6 | | 2.4 | | |
| | 80 | 1.9 | | | 0.2 | | 3.4 | | | 0.9 | |
| | 160 | 2.4 | | | | | 2.7 | | | | |
| C.86. | 0 | 50 | 100 | | | 0 | 50 | 100 | | |
| | 0 | 3.1 | 1.3 | 0.2 | | 2.0 | 0.5 | 0 | | |
| | 50 | 2.9 | 0.6 | | | 1.7 | 0.2 | | | |
| | 100 | 3.1 | | | | 1.6 | | | | |

TABLE III

LESION SCORES

| COMPOUND NO. | Eimeria acervulina* monensin | | | | | | Eimeria tenella* monensin | | | | | |
|---|---|---|---|---|---|---|---|---|---|---|---|---|
| C.1. | 0 | 20 | 40 | 80 | 120 | 160 | 0 | 20 | 40 | 80 | 120 | 160 |
| | 0 | 2.9 | 2.8 | 1.7 | 0.2 | 0 | 0 | 2.9 | 2.7 | 1.3 | 0.3 | 0.1 | 0 |
| | 40 | 3.1 | | 1.0 | 0.1 | | | 2.4 | | 1.3 | 0.6 | | |
| | 80 | 2.7 | | 1.1 | 0.1 | | | 2.0 | | 1.5 | 0.1 | | |
| | 120 | 2.9 | | | | | | 2.9 | | | | | |
| | 240 | 2.8 | | | | | | 2.6 | | | | | |
| C.5. | 0 | 20 | 40 | 80 | | | 0 | 20 | 40 | 80 | 120 | 160 |
| | 0 | 2.9 | 2.8 | 1.7 | 0.2 | | | 2.9 | 2.7 | 1.3 | 0.3 | 0.1 | 0 |
| | 20 | 2.8 | 2.8 | 1.0 | | | | 3.0 | 2.0 | 0.8 | | | |
| | 40 | 2.6 | 2.2 | 1.1 | 0.3 | | | 3.1 | 1.9 | 1.4 | 0.2 | | |
| | 80 | 2.9 | | | | | | 2.6 | | | | | |
| C.58. | 0 | 20 | 40 | 80 | 120 | 160 | 0 | 20 | 40 | 80 | 120 | 160 |
| | 0 | 2.9 | 2.8 | 1.7 | 0.2 | 0 | 0 | 2.9 | 2.7 | 1.3 | 0.3 | 0.1 | 0 |
| | 40 | 2.8 | | 0.2 | | | | 2.8 | | 0 | | | |
| C.76. | 0 | 20 | 40 | 80 | 120 | 160 | 0 | 20 | 40 | 80 | 120 | 160 |
| | 0 | 2.9 | 2.8 | 1.7 | 0.2 | 0 | 0 | 2.9 | 2.7 | 1.3 | 0.3 | 0.1 | 0 |
| | 40 | | | 1.5 | 0.2 | | | | | 1.9 | 0.2 | | |
| | 80 | | | 0.8 | 0.3 | | | | | 1.0 | 0.2 | | |
| | 160 | 3.0 | | | | | | 2.7 | | | | | |

*Infected with 1,000,000 oocysts of *Eimeria acervulina* and 250,000 oocysts of *Eimeria tenella*.

TABLE IV

LESION SCORES

| Compound Number | Eimeria acervulina* Eimeria maxima* (Intestinal) Monensin | | | | Eimerial tenella* (Cecal) Monensin | | | |
|---|---|---|---|---|---|---|---|---|
| | 0 | 25 | 50 | 100 | 0 | 25 | 50 | 100 |
| A.1. | 0 | 4.9 | 2.8 | .3 | 0 | 3.3 | 3.3 | .9 | 0 |
| | 25 | 3.7 | .3 | .07 | | 3.2 | .67 | .13 | |
| | 50 | 2.1 | 0 | 0 | | 2.7 | 0 | .07 | |
| | 100 | 1.3 | | | | .6 | | | |
| A.2. | 0 | 5.93 | 3.7 | 2.1 | 0 | 2.83 | 3.1 | 1.2 | .47 |
| | 25 | 1.72 | .33 | .13 | | 1.78 | .4 | 0 | |
| | 50 | .45 | 0 | 0 | | .55 | .2 | 0 | |
| | 100 | 0 | | | | 0 | | | |

*Infected with 500,000 oocysts of *Eimeria acervulina*, 60,000 oocysts of *Eimeria maxima*, and 40,000 oocysts of *Eimeria tenella*. Test conducted with three replicates.

We claim:

1. A process for controlling coccidiosis in poultry which comprises orally administering to the poultry a feedstuff comprising a first component which is a polyether antibiotic and a second component which is a carbanilide, said components being present in the feedstuff in concentrations which, in combination, exert a potentiated or synergized anticoccidial effect as to at least one coccidiosis-causing strain of Eimeria, and said carbanilide being selected from the group consisting of A.1. 3,3'-bis(trifluoromethyl)-4,4'-dichlorocarbanilide,
A.2. 3,3',5,5'-tetrakis(trifluoromethyl)carbanilide,
A.3. 3-chloro-4'-fluorocarbanilide,
A.4. 2-chloro-2'-fluorocarbanilide,
A.5. 3,4',5-tris(trifluoromethyl)carbanilide,
A.6. 3,4,5-trichlorocarbanilide,
A.7. 2-chloro-5-(trifluoromethyl)-4'-(ethoxycarbonyl)-carbanilide,
A.8. 2,6-dimethyl-4'-(N-methylacetamido)carbanilide,
A.9. 2-methoxy-4'-acetamidocarbanilide,
A.10. 3-(trifluoromethyl)-4'-iodothiocarbanilide,
A.12. 2-methoxy-4'-isopropylcarbanilide,
A.13. 2-methyl-2',5'-diethoxycarbanilide,
A.14. 4-ethyl-2'-methoxycarbanilide,
A.16. 2,4,4'-trimethyl-3'-nitrocarbanilide,
A.17. 2-amino-3-nitro-5-(trifluoromethyl)-2',4'-dimethylcarbanilide,
A.18. 2-amino-3,4'-dinitro-5-(trifluoromethyl)-2'-chlorocarbanilide,
A.19. 2-amino-3,5'-dinitro-5-(trifluoromethyl)-2'-fluorocarbanilide,
A.20. 2-amino-3-nitro-5-(trifluoromethyl)-2'-(ethoxycarbonyl)carbanilide,
A.21. 2-ethyl-6-sec-butylcarbanilide,
A.22. 2-isopropyl-2',4',6'-trimethylcarbanilide, A.23. 2-amino-3-nitro-3',5-bis(trifluoromethyl)-4'-chlorocarbanilide,
A.24 2-ethyl-6-sec-butyl-4'-n-butoxycarbanilide,
A.25. 2-amino-3-nitro-5-(trifluoromethyl)-2',4',5'-trichlorocarbanilide,
A.26. 2-amino-3,3'-dinitro-5-(trifluoromethyl)-4'-chlorocarbanilide,
A.27. 2-amino-3-nitro-5-(trifluoromethyl)-2'-methyl-4'-bromocarbanilide,
A.28. 2-amino-3-nitro-5-(trifluoromethyl)-2',6'-dibromo-4'-fluorocarbanilide,
A.30. 3,3',5,5'-tetrakis(trifluoromethyl)thiocarbanilide,
A.31. 2,4-dimethoxy-4'-(ethoxycarbonyl)carbanilide,
A.32. 4-(ethoxycarbonyl)-2'-methyl-6'-ethylcarbanilide,
A.33. 2,2'-dinitro-4,4'-bis(trifluoromethyl)carbanilide,
A.34. 3,3',4,4',5,5'-hexachlorocarbanilide,
A.35. 3-nitro-4-chloro-4'-(trifluoromethyl)carbanilide,
A.36. 4-chloro-3,4'-bis(trifluoromethyl)carbanilide,
A.37. 4,4'-dinitro-2,2'-bis(trifluoromethyl)carbanilide,
A.38. 4,4'-bis(trifluoromethyl)carbanilide,
A.39. 3-bromo-3',5'-dimethylcarbanilide,
A.40. 2,5-dichloro-4'-methyl-$N^2$-ethylcarbanilide,
A.41. 2,5-dichloro-2',4'-difluorocarbanilide,
A.43. 2,6-diethyl-4'-(ethoxycarbonyl)carbanilide,
A.44. 3-ethyl-3'-chloro-4'-methyl-$N^2$-ethylcarbanilide,
A.45. 2,6-dimethyl-4'-(ethoxycarbonyl)carbanilide,
A.46. 4-methoxy-3'-acetamidocarbanilide,
A.47. 2-methoxy-4'-(n-butoxycarbonyl)carbanilide,
A.48. 4-(isobutoxycarbonyl)carbanilide,
A.49. 2,4'-bis(methoxycarbonyl)carbanilide,
A.50. 2',4-dichloro-3-nitro-3'-(trifluoromethyl)carbanilide,
A.51. 3,4,4',5-tetrachloro-3'-(trifluoromethyl)carbanilide,
A.52. 4-chloro-3-nitro-3',5'-bis(trifluoromethyl)carbanilide,
A.53. 2,4,6-trimethyl-4'-(ethoxycarbonyl)carbanilide,
A.54. 2-(trifluoromethyl)-2'-ethyl-6'-isopropylcarbanilide,
A.55. 4-chloro-3,3',5'-tris(trifluoromethyl)carbanilide,
A.56. 3,4,4',5-tetrachloro-3'-nitrocarbanilide,
A.57. 2,6-dimethyl-4'-benzoylcarbanilide,
A.58. 3,4-dimethyl-2'-ethoxycarbanilide,
A.59. 2-chloro-4,4'-bis(methylthio)carbanilide,
A.63. 4-(trifluoromethyl)-4'-nitrocarbanilide, and
A.64. 3,3',5,5'-tetrakis(trifluoromethyl)-N,N'-dimethylcarbanilide,
B. A compound of the formula

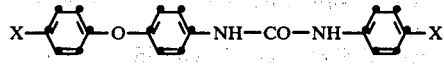

Formula I wherein each X is independently selected from the group consisting of chlorine, bromine, and nitro radicals; or a compound of the same formula as (I) except that a hydrogen of at least one of the rings of (I) is replaced by a substituent selected from the group consisting of chlorine, bromine, nitro and lower alkyl radicals; or
C. A compound selected from the group consisting of
C.1. 3,3',5'-tris(trifluoromethyl)-4-methoxycarbanilide,
C.2. 3-(trifluoromethoxy)-3',5'-bis(trifluoromethyl)carbanilide,
C.3. 4-(trifluoromethoxy)-3',5'-bis(trifluoromethyl)carbanilide,
C.4. 2,3',5'-tris(trifluoromethyl)-4-(trifluoromethoxy)carbanilide,
C.5. 4-(methylthio)-3',5'-bis(trifluoromethyl)carbanilide,
C.7. 3-chloro-4-(methylthio)-3',5'-bis(trifluoromethyl)carbanilide,
C.8. 3-(trifluoromethylthio)-3',5'-bis(trifluoromethyl)carbanilide,
C.9. 4-(trifluoromethylthio)-3',5'-bis(trifluoromethyl)carbanilide,
C.10. 2-chloro-4-(trifluoromethylthio)-3',5'-bis(trifluoromethyl)carbanilide,
C.11. 4-(trifluoromethylthio)-3'-(trifluoromethyl)-5'-nitrocarbanilide,
C.12. 4-(trifluoromethylthio)-2',5'-bis(trifluoromethyl)-4'-nitrocarbanilide,
C.13. 4,4'-bis(trifluoromethylthio)carbanilide,
C.14. 4-(trifluoromethylthio)-4'-(chloromethylsulfonyl)carbanilide,
C.15. 3-(difluoromethylthio)-3',5'-bis(trifluoromethyl)carbanilide,
C.16. 4-(ethylthio)-3',5'-bis(trifluoromethyl)carbanilide,
C.17. 3-chloro-4-(ethylthio)-3',5'-bis(trifluoromethyl)carbanilide,
C.18. 4-ethoxy-3,3',5'-tris(trifluoromethyl)carbanilide,
C.19. 3-(trifluoromethyl)-4-ethoxy-4'-(trifluoromethylthio)carbanilide,
C.20. 3-(trifluoromethyl)-4-ethoxy-3'-(trifluoromethylthio)carbanilide,
C.21. 4-methyl-3-(2-chloroethoxy)-3',5'-bis(trifluoromethyl)carbanilide,
C.22. 4-(1,2-dichlorovinyloxy)-3'-(trifluoromethyl)-4'-chlorocarbanilide,
C.23. 4-(1,2-dichlorovinyloxy)-3',5'-bis(trifluoromethyl)carbanilide,
C.24. 4-(2,2,2-trichloro-1,1-difluoroethoxy)-3',5'-bis(trifluoromethyl)carbanilide,
C.25. 2-(2,2-dichloro-1,1-difluoroethoxy)-3',5'-bis(trifluoromethyl)carbanilide,
C.26. 3-(2,2-dichloro-1,1-difluoroethoxy)-3',5'-bis(trifluoromethyl)carbanilide,
C.27. 3-(2,2-dichloro-1,1-difluoroethoxy)-4-bromo-3',5'-bis(trifluoromethyl)carbanilide,
C.28. 4-(2,2-dichloro-1,1-difluoroethoxy)-3',5'-bis(trifluoromethyl)carbanilide,
C.29. 4-(2,2-dichloro-1,1-difluoroethoxy)-3'-(trifluoromethyl)-4'-chlorocarbanilide,
C.30. 3-methoxy-4-(2,2-dichloro-1,1-difluoroethoxy)-3',5'-bis(trifluoromethyl)carbanilide,
C.31. 3-methyl-4-(2,2-dichloro-1,1-difluoroethoxy)-3',5'-bis(trifluoromethyl)carbanilide,
C.32. 3-methyl-4-(2,2-dichloro-1,1-difluoroethoxy)-4'-isopropylcarbanilide,
C.33. 3-nitro-4-(2,2-dichloro-1,1-difluoroethoxy)-3',5'-bis(trifluoromethyl)carbanilide,
C.34. 2-(2-chloro-1,1,2-trifluoroethoxy)-3',5'-bis(trifluoromethyl)carbanilide,
C.35. 4-(2,2-dichloro-1,1-difluoroethoxy)-3,3',5'-tris(trifluoromethyl)carbanilide,
C.36. 3-(2-chloro-1,1,2-trifluoroethoxy)-3',5'-bis(trifluoromethyl)carbanilide,
C.37. 4-(2-chloro-1,1,2-trifluoroethoxy)-3',5'-bis(trifluoromethyl)carbanilide,
C.38. 4-(2-chloro-1,1,2-trifluoroethoxy)-3',5'-bis(trifluoromethyl)thiocarbanilide,
C.39. 4-(2-chloro-1,1,2-trifluoroethoxy)-3'-(trifluoromethyl)-5'-nitrocarbanilide,
C.40. 4,4'-bis(2-chloro-1,1,2-trifluoroethoxy)carbanilide, C.41. 4-(2-chloro-1,1,2-trifluoroethoxy)-4'-(trifluoromethylthio)carbanilide,
C.42. 4-(2-chloro-1,1,2-trifluoroethoxy)-3'-(trifluoromethyl)-4'-chlorocarbanilide,
C.43. 4-(2-chloro-1,1,2-trifluoroethoxy)-3,3'-bis(trifluoromethyl)-5'-nitrocarbanilide,
C.44. 4-(2-chloro-1,1,2-trifluoroethoxy)-3,3',5'-tris(trifluoromethyl)carbanilide,
C.45. 3-(1,1,2-trifluoroethoxy)-3',5'-bis(trifluoromethyl)carbanilide,
C.46. 3-(1,1,2,2-tetrafluoroethoxy)-3',5'-bis(trifluoromethyl)carbanilide,
C.47. 3-methyl-4-(1,1,2,2-tetrafluoroethoxy)-3'-(chlorodifluoromethyl)carbanilide,
C.48. 3-methyl-4-(1,1,2,2-tetrafluoroethoxy)-3'-(trifluoromethyl)-4'-chlorocarbanilide,
C.49. 3-(trifluoromethyl)-4-(1,1,2,2-tetrafluoroethoxy)-4'-bromocarbanilide,
C.50. 3-(1,1,2,3,3,3-hexafluoro-n-propoxy)-3',5'-bis(trifluoromethyl)carbanilide,
C.51. 4-(1,1,2,3,3,3-hexafluoro-n-propoxy)-3',5'-bis(trifluoromethyl)carbanilide,
C.52. 3-chloro-4-(1,1,2,3,3,3-hexafluoro-n-propoxy)-3',5'-bis(trifluoromethyl)carbanilide,
C.53. 3-methyl-4-(1,1,2,3,3,3-hexafluoro-n-propoxy)-3',5'-bis(trifluoromethyl)carbanilide,
C.54. 4-(1,1,2,3,3,3-hexafluoro-n-propoxy)-3,3',5'-tris(trifluoromethyl)carbanilide,
C.55. 4-(1,1,2,3,3,3-hexafluoro-n-propoxy)-3,3'-bis(trifluoromethyl)-5'-nitrocarbanilide,
C.56. 4-(methoxycarbonylthio)-3',5'-bis(trifluoromethyl)carbanilide,
C.57. 4-(4-chlorophenoxy)-4'-(trifluoromethylthio)thiocarbanilide,
C.58. 4-(4-chlorophenoxy)-3',5'-bis(trifluoromethyl)carbanilide,
C.59. 3-chloro-4-(4-chlorophenoxy)-3',5'-bis(trifluoromethyl)carbanilide,
C.60. 4-(4-chlorophenoxy)-3'-(trifluoromethyl)-5'-nitrocarbanilide,
C.61. 4-(3,5-bis(trifluoromethyl)phenoxy)-3',5'-bis(trifluoromethyl)carbanilide,
C.63. 4-(4-methylphenoxycarbonyl)-4'-(trifluoromethylthio)carbanilide,
C.64. 3,5-bis(trifluoromethyl)-2',4',6'-trichlorocarbanilide,
C.65. 3,5-bis(trifluoromethyl)-2',4',5'-trichlorocarbanilide,
C.66. 3,3'-bis(trifluoromethyl)-5'-nitrocarbanilide,
C.67. 3,3',5-tris(trifluoromethyl)-5'-nitrocarbanilide,
C.68. 2',3,5,6'-tetrakis(trifluoromethyl)-4'-nitrocarbanilide,
C.69. 3-(chlorodifluoromethyl)-3',5'-bis(trifluoromethyl)carbanilide,
C.70. 3-(1,1,2,2-tetrafluoroethyl)-3',5'-bis(trifluoromethyl)carbanilide,
C.71. 4-phenyl-3',5'-bis(trifluoromethyl)carbanilide,
C.72. 3-(fluorosulfonyl)-3',5'-bis(trifluoromethyl)carbanilide,
C.73. 4-(fluorosulfonyl)-4'-(trifluoromethylthio)carbanilide,
C.74. 4-(fluorosulfonyl)-3'-(trifluoromethyl)-5'-nitrocarbanilide,
C.75. 4-(chloromethylsulfonyl)-3',5'-bis(trifluoromethyl)carbanilide,
C.76. 2-(ethylsulfonyl)-3',5,5'-tris(trifluoromethyl)carbanilide,
C.77. 2-(ethylsulfonyl)-3',5-bis(trifluoromethyl)-5'-nitrocarbanilide,
C.78. 4-(trifluoromethylsulfonyl)-3',5'-bis(trifluoromethyl)carbanilide,
C.79. 4-(trifluoromethylsulfonyl)-3'-(trifluoromethyl)-4'-methoxycarbanilide,
C.80. 4-(trifluoromethylsulfonyl)-4'-(trifluoromethylthio)carbanilide,
C.81. 4-(4-nitrophenylsulfonyl)-4'-(trifluoromethylthio)carbanilide,
C.82. 4-(4-acetamidophenylsulfonyl)-4'-(trifluoromethylthio)carbanilide,
C.83. 4-(4-(isopropylideneamino)phenylsulfonyl)-4'-(trifluoromethylthio)carbanilide,
C.84. 4,4-sulfonylbis(3'-(trifluoromethylthio)carbanilide),
C.85. 4,4-sulfonylbis(4'-(1,2-dichlorovinyloxy)carbanilide),
C.86. 4,4-sulfonylbis(3'-(1,1,2,2-tetrafluoroethoxy)carbanilide),
C.87. 4,4-sulfonylbis(4'-(2-chloro-1,1,2-trifluoroethoxy)carbanilide), and
C.88. 4,4-sulfonylbis(4'-(trifluoromethylthio)carbanilide).

2. The process of claim 1 wherein the polyether antibiotic is selected from the group consisting of monensin, narasin, lasalocid, salinomycin, A-204, lonomycin, X-206, nigericin, and dianemycin.

3. The process of claim 2 wherein the second component is selected from the group consisting of compounds A.1. through A.10., A.12. through A.14., A.16. through A.28., A.30. through A.41., A.43. through A.59., A.63. and A.64.

4. The process of claim 3 wherein the polyether antibiotic is monensin.

5. The process of claim 4 wherein the second component is 3,3'-bis(trifluoromethyl)-4,4'-dichlorocarbanilide.

6. The process of claim 4 wherein the second component is 3,3',5,5'-tetrakis(trifluoromethyl)carbanilide.

7. The process of claim 3 wherein the polyether antibiotic is narasin.

8. The process of claim 7 wherein the second component is 3,3'-bis(trifluoromethyl)-4,4'-dichlorocarbanilide.

9. The process of claim 7 wherein the second component is 3,3',5,5'-tetrakis(trifluoromethyl)carbanilide.

10. The process of claim 2 wherein the second component is a compound as defined in section B.

11. The process of claim 10 wherein the second component is 4-nitro-3'-chloro-4'-(4-chlorophenoxy)carbanilide.

12. The process of claim 10 wherein the second component is 4-nitro-3'-chloro-4'-(4-chlorophenoxy)carbanilide.

13. The process of claim 10 wherein the second component is 4-nitro-3'-bromo-4'-(4-bromophenoxy)carbanilide.

14. The process of claim 2 wherein the second component is selected from the group consisting of compounds C.1. through C.5., C.7. through C.61, and C.63. through C.88.

15. The process of claim 14 wherein the second component is 4,4'-bis(trifluoromethylthio)carbanilide.

16. The process of claim 14 wherein the second component is 4-(4-chlorophenoxy)-3',5'-bis(trifluoromethyl)carbanilide.

17. The process of claim 14 wherein the second component is 3,5-bis(trifluoromethy)-2',4',5'-trichlorocarbanilide.

18. The process of claim 14 wherein the second component is 4,4-sulfonylbis(3'-(1,1,2,2-tetrafluoroethoxy)-carbanilide).

19. The process of claim 2 wherein the polyether antibiotic is narasin.

20. The process of claim 2 wherein the polyether antibiotic is lasalocid.

21. The process of claim 2 wherein the polyether antibiotic is salinomycin.

22. The process of claim 2 wherein the polyether antibiotic is A-204.

23. The process of claim 2 wherein the polyether antibiotic is lonomycin.

24. The process of claim 2 wherein the polyether antibiotic is X-206.

25. The process of claim 2 wherein the polyether antibiotic is nigericin.

26. The process of claim 2 wherein the polyether antibiotic is dianemycin.

27. A poultry feedstuff composition comprising a first component which is a polyether antibiotic and a second component which is a carbanilide, said components being present in concentrations which, in combination, exert a potentiated or synergized anticoccidial effect as to at least one coccidiosis-causing strain of Eimeria, and said carbanilide being selected from the group consisting of A.1. 3,3'-bis(trifluoromethyl)-4,4'-dichlorocarbanilide,
A.2. 3,3',5,5'-tetrakis(trifluoromethyl)carbanilide,
A.3. 3-chloro-4'-fluorocarbanilide,
A.4. 2-chloro-2'-fluorocarbanilide,
A.5. 3,4',5-tris(trifluoromethyl)carbanilide,
A.6. 3,4,5-trichlorocarbanilide,
A.7. 2-chloro-5-(trifluoromethyl)-4'-(ethoxycarbonyl)carbanilide,
A.8. 2,6-dimethyl-4'-(N-methylacetamido)carbanilide,
A.9. 2-methoxy-4'-acetamidocarbanilide,
A.10. 3-(trifluoromethyl)-4'-iodothiocarbanilide,
A.12. 2-methoxy-4'-isopropylcarbanilide,
A.13. 2-methyl-2',5'-diethoxycarbanilide,
A.14. 4-ethyl-2'-methoxycarbanilide,
A.16. 2,4,4'-trimethyl-3'-nitrocarbanilide,
A.17. 2-amino-3-nitro-5-(trifluoromethyl)-2',4'-dimethylcarbanilide,
A.18. 2-amino-3,4'-dinitro-5-(trifluoromethyl)-2'-chlorocarbanilide,
A.19. 2-amino-3,5'-dinitro-5-(trifluoromethyl)-2'-fluorocarbanilide,
A.20. 2-amino-3-nitro-5-(trifluoromethyl)-2'-(ethoxycarbonyl)carbanilide,
A.21. 2-ethyl-6-sec-butylcarbanilide,
A.22. 2-isopropyl-2',4',6'-trimethylcarbanilide,
A.23. 2-amino-3-nitro-3',5-bis(trifluoromethyl)-4'-chlorocarbanilide,
A.24. 2-ethyl-6-sec-butyl-4'-n-butoxycarbanilide,
A.25. 2-amino-3-nitro-5-(trifluoromethyl)-2',4',5'-trichlorocarbanilide,
A.26. 2-amino-3,3'-dinitro-5-(trifluoromethyl)-4'-chlorocarbanilide,
A.27. 2-amino-3-nitro-5-(trifluoromethyl)-2'-methyl-4'-bromocarbanilide,
A.28. 2-amino-3-nitro-5-(trifluoromethyl)-2',6'-dibromo-4'-fluorocarbanilide,
A.30. 3,3',5,5'-tetrakis(trifluoromethyl)thiocarbanilide,
A.31. 2,4-dimethoxy-4'-(ethoxycarbonyl)carbanilide,
A.32. 4-(ethoxycarbonyl)-2'-methyl-6'-ethylcarbanilide,
A.33. 2,2'-dinitro-4,4'-bis(trifluoromethyl)carbanilide,
A.34. 3,3',4,4',5,5'-hexachlorocarbanilide,
A.35. 3-nitro-4-chloro-4'-(trifluoromethyl)carbanilide,
A.36. 4-chloro-3,4'-bis(trifluoromethyl)carbanilide,
A.37. 4,4'-dinitro-2,2'-bis(trifluoromethyl)carbanilide,
A.38. 4,4'-bis(trifluoromethyl)carbanilide,
A.39. 3-bromo-3',5'-dimethylcarbanilide,
A.40. 2,5-dichloro-4'-methyl-$N^2$-ethylcarbanilide,
A.41. 2,5-dichloro-2',4'-difluorocarbanilide,
A.43. 2,6-diethyl-4'-(ethoxycarbonyl)carbanilide,
A.44. 3-ethyl-3'-chloro-4'-methyl-$N^2$-ethylcarbanilide,
A.45. 2,6-dimethyl-4'-(ethoxycarbonyl)carbanilide,
A.46. 4-methoxy-3'-acetamidocarbanilide,
A.47. 2-methoxy-4'-(n-butoxycarbonyl)carbanilide,
A.48. 4-(isobutoxycarbonyl)carbanilide,
A.49. 2,4'-bis(methoxycarbonyl)carbanilide,
A.50. 2',4'-dichloro-3-nitro-3'-(trifluoromethyl)carbanilide,
A.51. 3,4,4',5-tetrachloro-3'-(trifluoromethyl)carbanilide,
A.52. 4-chloro-3-nitro-3',5'-bis(trifluoromethyl)carbanilide,
A.53. 2,4,6-trimethyl-4'-(ethoxycarbonyl)carbanilide,
A.54. 2-(trifluoromethyl)-2'-ethyl-6'-isopropylcarbanilide,
A.55. 4-chloro-3,3',5'-tris(trifluoromethyl)carbanilide,
A.56. 3,4,4',5-tetrachloro-3'-nitrocarbanilide,
A.57. 2,6-dimethyl-4'-benzoylcarbanilide,
A.58. 3,4-dimethyl-2'-ethoxycarbanilide,
A.59. 2-chloro-4,4'-bis(methylthio)carbanilide,
A.63. 4-(trifluoromethyl)-4'-nitrocarbanilide, and
A.64. 3,3',5,5'-tetrakis(trifluoromethyl)-N,N'-dimethylcarbanilide, B. A compound of the formula

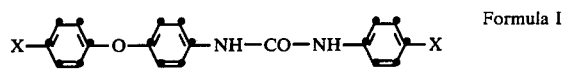

Formula I wherein each X is independently selected from the group consisting of chlorine, bromine, and nitro radicals; or a compound of the same formula as (I) except that a hydrogen of at least one of the rings of (I) is replaced by a substituent selected from the group consisting of chlorine, bromine, nitro and lower alkyl radicals; or C. A compound selected from the group consisting of
C.1. 3,3',5'-tris(trifluoromethyl)-4-methoxycarbanilide,
C.2. 3-(trifluoromethoxy)-3',5'-bis(trifluoromethyl)carbanilide,
C.3. 4-(trifluoromethoxy)-3',5'-bis(trifluoromethyl)carbanilide,
C.4. 2,3',5'-tris(trifluoromethyl)-4-(trifluoromethoxy)carbanilide,
C.5. 4-(methylthio)-3',5'-bis(trifluoromethyl)carbanilide,
C.7. 3-chloro-4-(methylthio)-3',5'-bis(trifluoromethyl)carbanilide,
C.8. 3-(trifluoromethylthio)-3',5'-bis(trifluoromethyl)carbanilide,
C.9. 4-(trifluoromethylthio)-3',5'-bis(trifluoromethyl)carbanilide,
C.10. 2-chloro-4-(trifluoromethylthio)-3',5'-bis(trifluoromethyl)carbanilide,
C.11. 4-(trifluoromethylthio)-3'-(trifluoromethyl)-5'-nitrocarbanilide, C.12. 4-(trifluoromethylthio)-2',5'-bis(trifluoromethyl)-4'-nitrocarbanilide,
C.13. 4,4'-bis(trifluoromethylthio)carbanilide,
C.14. 4-(trifluoromethylthio)-4'-(chloromethylsulfonyl)carbanilide,
C.15. 3-(difluoromethylthio)-3',5'-bis(trifluoromethyl)carbanilide,
C.16. 4-(ethylthio)-3',5'-bis(trifluoromethyl)carbanilide,
C.17. 3-chloro-4-(ethylthio)-3',5'-bis(trifluoromethyl)carbanilide,
C.18. 4-ethoxy-3,3',5'-tris(trifluoromethyl)carbanilide,
C.19. 3-(trifluoromethyl)-4-ethoxy-4'-(trifluoromethylthio)carbanilide,
C.20. 3-(trifluoromethyl)-4-ethoxy-3'-(trifluoromethylthio)carbanilide,
C.21. 4-methyl-3-(2-chloroethoxy)-3',5'-bis(trifluoromethyl)carbanilide,
C.22. 4-(1,2-dichlorovinyloxy)-3'-(trifluoromethyl)-4'-chlorocarbanilide,
C.23. 4-(1,2-dichlorovinyloxy)-3',5'-bis(trifluoromethyl)carbanilide,
C.24. 4-(2,2,2-trichloro-1,1-difluoroethoxy)-3',5'-bis(trifluoromethyl)carbanilide,
C.25. 2-(2,2-dichloro-1,1-difluoroethoxy)-3',5'-bis(trifluoromethyl)carbanilide,
C.26. 3-(2,2-dichloro-1,1-difluoroethoxy)-3',5'-bis(trifluoromethyl)carbanilide,
C.27. 3-(2,2-dichloro-1,1-difluoroethoxy)-4-bromo-3',5'-bis(trifluoromethyl)carbanilide,
C.28. 4-(2,2-dichloro-1,1-difluoroethoxy)-3',5'-bis(trifluoromethyl)carbanilide,
C.29. 4-(2,2-dichloro-1,1-difluoroethoxy)-3'-(trifluoromethyl)-4'-chlorocarbanilide,
C.30. 3-methoxy-4-(2,2-dichloro-1,1-difluoroethoxy)-3',5'-bis(trifluoromethyl)carbanilide,
C.31. 3-methyl-4-(2,2-dichloro-1,1-difluoroethoxy)-3',5'-bis(trifluoromethyl)carbanilide,
C.32. 3-methyl-4-(2,2-dichloro-1,1-difluoroethoxy)-4'-isopropylcarbanilide,
C.33. 3-nitro-4-(2,2-dichloro-1,1-difluoroethoxy)-3',5'-bis(trifluoromethyl)carbanilide,
C.34. 2-(2-chloro-1,1,2-trifluoroethoxy)-3',5'-bis(trifluoromethyl)carbanilide,
C.35. 4-(2,2-dichloro-1,1-difluoroethoxy)-3,3',5'-tris(trifluoromethyl)carbanilide,
C.36. 3-(2-chloro-1,1,2-trifluoroethoxy)-3',5'-bis(trifluoromethyl)carbanilide,
C.37. 4-(2-chloro-1,1,2-trifluoroethoxy)-3',5'-bis(trifluoromethyl)carbanilide,
C.38. 4-(2-chloro-1,1,2-trifluoroethoxy)-3',5'-bis(trifluoromethyl)thiocarbanilide,
C.39. 4-(2-chloro-1,1,2-trifluoroethoxy)-3'-(trifluoromethyl)-5'-nitrocarbanilide,
C.40. 4,4'-bis(2-chloro-1,1,2-trifluoroethoxy)carbanilide,
C.41. 4-(2-chloro-1,1,2-trifluoroethoxy)-4'-(trifluoromethylthio)carbanilide,
C.42. 4-(2-chloro-1,1,2-trifluoroethoxy)-3'-(trifluoromethyl)-4'-chlorocarbanilide,
C.43. 4-(2-chloro-1,1,2-trifluoroethoxy)-3,3'-bis(trifluoromethyl)-5'-nitrocarbanilide,
C.44. 4-(2-chloro-1,1,2-trifluoroethoxy)-3,3',5'-tris(trifluoromethyl)carbanilide,
C.45. 3-(1,1,2-trifluoroethoxy)-3',5'-bis(trifluoromethyl)carbanilide,
C.46. 3-(1,1,2,2-tetrafluoroethoxy)-3',5'-bis(trifluoromethyl)carbanilide,
C.47. 3-methyl-4-(1,1,2,2-tetrafluoroethoxy)-3'-(chlorodifluoromethyl)carbanilide,
C.48. 3-methyl-4-(1,1,2,2-tetrafluoroethoxy)-3'-(trifluoromethyl)-4'-chlorocarbanilide,
C.49. 3-(trifluoromethyl)-4-(1,1,2,2-tetrafluoroethoxy)-4'-bromocarbanilide,
C.50. 3-(1,1,2,3,3,3-hexafluoro-n-propoxy)-3',5'-bis(trifluoromethyl)carbanilide,
C.51. 4-(1,1,2,3,3,3-hexafluoro-n-propoxy)-3',5'-bis(trifluoromethyl)carbanilide,
C.52. 3-chloro-4-(1,1,2,3,3,3-hexafluoro-n-propoxy)-3',5'-bis(trifluoromethyl)carbanilide,
C.53. 3-methyl-4-(1,1,2,3,3,3-hexafluoro-n-propoxy)-3',5'-bis(trifluoromethyl)carbanilide,
C.54. 4-(1,1,2,3,3,3-hexafluoro-n-propoxy)-3,3',5'-tris(trifluoromethyl)carbanilide,
C.55. 4-(1,1,2,3,3,3-hexafluoro-n-propoxy)-3,3'-bis(trifluoromethyl)-5'-nitrocarbanilide,
C.56. 4-(methoxycarbonylthio)-3',5'-bis(trifluoromethyl)carbanilide,
C.57. 4-(4-chlorophenoxy)-4'-(trifluoromethylthio)thiocarbanilide,
C.58. 4-(4-chlorophenoxy)-3',5'-bis(trifluoromethyl)carbanilide,
C.59. 3-chloro-4-(4-chlorophenoxy)-3',5'-bis(trifluoromethyl)carbanilide,
C.60. 4-(4-chlorophenoxy)-3'-(trifluoromethyl)-5'-nitrocarbanilide,
C.61. 4-(3,5-bis(trifluoromethyl)phenoxy)-3',5'-bis(trifluoromethyl)carbanilide,
C.63. 4-(4-methylphenoxycarbonyl)-4'-(trifluoromethylthio)carbanilide,
C.64. 3,5-bis(trifluoromethyl)-2',4',6'-trichlorocarbanilide,
C.65. 3,5-bis(trifluoromethyl)-2',4',5'-trichlorocarbanilide,
C.66. 3,3'-bis(trifluoromethyl)-5'-nitrocarbanilide,
C.67. 3,3',5-tris(trifluoromethyl)-5'-nitrocarbanilide,
C.68. 2',3,5,6'-tetrakis(trifluoromethyl)-4'-nitrocarbanilide,
C.69. 3-(chlorodifluoromethyl)-3',5'-bis(trifluoromethyl)carbanilide,
C.70. 3-(1,1,2,2-tetrafluoroethyl)-3',5'-bis(trifluoromethyl)carbanilide,
C.71. 4-phenyl-3',5'-bis(trifluoromethyl)carbanilide,
C.72. 3-(fluorosulfonyl)-3',5'-bis(trifluoromethyl)carbanilide,
C.73. 4-(fluorosulfonyl)-4'-(trifluoromethylthio)carbanilide,
C.74. 4-(fluorosulfonyl)-3'-(trifluoromethyl)-5'-nitrocarbanilide,
C.75. 4-(chloromethylsulfonyl)-3',5'-bis(trifluoromethyl)carbanilide,
C.76. 2-(ethylsulfonyl)-3',5,5'-tris(trifluoromethyl)carbanilide,
C.77. 2-(ethylsulfonyl)-3',5-bis(trifluoromethyl)-5'-nitrocarbanilide,
C.78. 4-(trifluoromethylsulfonyl)-3',5'-bis(trifluoromethyl)carbanilide,
C.79. 4-(trifluoromethylsulfonyl)-3'-(trifluoromethyl)-4'-methoxycarbanilide,
C.80. 4-(trifluoromethylsulfonyl)-4'-(trifluoromethylthio)carbanilide,
C.81. 4-(4-nitrophenylsulfonyl)-4'-(trifluoromethylthio)carbanilide,
C.82. 4-(4-acetamidophenylsulfonyl)-4'-(trifluoromethylthio)carbanilide, C.83. 4-(4-(isopropylideneamino)phenylsulfonyl)-4'-(trifluoromethylthio)carbanilide,
C.84 4,4-sulfonylbis(3'-(trifluoromethylthio)carbanilide),
C.85. 4,4-sulfonylbis(4'-(1,2-dichlorovinyloxy)carbanilide),
C.86. 4,4-sulfonylbis(3'-(1,1,2,2-tetrafluoroethoxy)carbanilide),
C.87. 4,4-sulfonylbis(4'-(2-chloro-1,1,2-trifluoroethoxy) carbanilide), and
C.88. 4,4-sulfonylbis(4'-(trifluoromethylthio)carbanilide).

28. The composition of claim 27 wherein the polyether antibiotic is selected from the group consisting of monensin, narasin, lasalocid, salinomycin, A-204, lonomycin, X-206, nigericin, and dianemycin.

29. The composition of claim 28 wherein the second component is selected from the group consisting of compounds A.1. through A.10., A.12. through A.14., A.16. through A.28., A.30. through A.41., A.43. through A.59., A.63., and A.64.

30. The composition of claim 29 wherein the polyether antibiotic is monensin.

31. The composition of claim 30 wherein the second component is 3,3'-bis(trifluoromethyl)-4,4'-dichlorocarbanilide.

32. The composition of claim 31 wherein the second component is 3,3',5,5'-tetrakis(trifluoromethyl)carbanilide.

33. The composition of claim 29 wherein the polyether antibiotic is narasin.

34. The composition of claim 33 wherein the second component is 3,3'-bis(trifluoromethyl)-4,4'-dichlorocarbanilide.

35. The composition of claim 33 wherein the second component is 3,3',5,5'-tetrakis(trifluoromethyl)carbanilide.

36. The composition of claim 28 wherein the second component is a compound as defined in section B.

37. The composition of claim 36 wherein the second component is 4-nitro-3'-chloro-4'-(4-chlorophenoxy)-carbanilide.

38. The composition of claim 36 wherein the second component is 4-nitro-3'-chloro-4'-(4-chlorophenoxy)-carbanilide.

39. The composition of claim 36 wherein the second component is 4-nitro-3'-bromo-4'-(4-bromophenoxy)-carbanilide.

40. The composition of claim 28 wherein the second component is selected from the group consisting of compounds C.1. through C.5., C.7. through C.61., and C.63. through C.88.

41. The composition of claim 40 wherein the second component is 4,4'-bis(trifluoromethylthio)carbanilide.

42. The composition of claim 40 wherein the second component is 4-(4-chlorophenoxy)-3',5'-bis(trifluoromethyl)carbanilide.

43. The composition of claim 40 wherein the second component is 3,5-bis(trifluoromethyl)-2',4',5'-trichlorocarbanilide.

44. The composition of claim 40 wherein the second component is 4,4-sulfonylbis(3'-(1,1,2,2-tetrafluoroethoxy)carbanilide).

45. The composition of claim 28 wherein the polyether antibiotic is narasin.

46. The composition of claim 28 wherein the polyether antibiotic is lasalocid.

47. The composition of claim 28 wherein the polyether antibiotic is salinomycin.

48. The composition of claim 28 wherein the polyether antibiotic is A-204.

49. The composition of claim 28 wherein the polyether antibiotic is lonomycin.

50. The composition of claim 28 wherein the polyether antibiotic is X-206.

51. The composition of claim 28 wherein the polyether antibiotic is nigericin.

52. The composition of claim 28 wherein the polyether antibiotic is dianemycin.

* * * * *